(12) United States Patent
Chand et al.

(10) Patent No.: US 10,851,376 B2
(45) Date of Patent: Dec. 1, 2020

(54) LONG NONCODING RNAS IN PULMONARY AIRWAY INFLAMMATION

(71) Applicants: Hitendra S. Chand, Doral, FL (US); Madhavan Nair, Coral Gables, FL (US)

(72) Inventors: Hitendra S. Chand, Doral, FL (US); Madhavan Nair, Coral Gables, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 16/668,781

(22) Filed: Oct. 30, 2019

(65) Prior Publication Data

US 2020/0208153 A1 Jul. 2, 2020

Related U.S. Application Data

(60) Provisional application No. 62/785,887, filed on Dec. 28, 2018.

(51) Int. Cl.
 C12N 15/113 (2010.01)
 A61K 31/7105 (2006.01)

(52) U.S. Cl.
 CPC ........ *C12N 15/113* (2013.01); *A61K 31/7105* (2013.01); *C12N 2310/11* (2013.01); *C12N 2310/14* (2013.01)

(58) Field of Classification Search
 CPC .............. A01K 2207/05; C12N 15/113; C12N 2310/14
 See application file for complete search history.

(56) References Cited

U.S. PATENT DOCUMENTS

| | | | |
|---|---|---|---|
| 9,410,206 B2 | 8/2016 | Hoon et al. | |
| 9,822,359 B1 | 11/2017 | Cooper et al. | |
| 9,856,479 B2 | 1/2018 | Lee et al. | |
| 9,862,943 B1 | 1/2018 | Kim et al. | |
| 2005/0192239 A1* | 9/2005 | Roth | C12Q 1/6886 514/44 A |
| 2006/0014166 A1* | 1/2006 | Cohen | C07K 14/47 435/6.17 |
| 2013/0178428 A1* | 7/2013 | Hoon | C12Q 1/6886 514/19.3 |
| 2018/0044672 A1 | 2/2018 | Zehendner et al. | |
| 2018/0080084 A1 | 3/2018 | Zheng et al. | |
| 2020/0024603 A1* | 1/2020 | Aznarez | C12N 15/113 |

FOREIGN PATENT DOCUMENTS

| | | |
|---|---|---|
| CN | 106047875 A | 10/2016 |
| CN | 106480176 A | 3/2017 |
| CN | 106676110 A | 5/2017 |
| CN | 106701900 A | 5/2017 |
| CN | 106987651 A | 7/2017 |
| CN | 107043823 A | 8/2017 |
| WO | 2016197592 A1 | 12/2016 |

OTHER PUBLICATIONS

Austin, P.J., et al., "Transcriptional profiling identifies the long noncoding RNA plasmacytoma variant translocation (PVT1) as a novel regulator of the asthmatic phenotype in human airway smooth muscle." J Allergy Clin Immunol, Mar. 2017, 139(3): 780-789.
Guo, W., et al., "ICAM-1-Related Noncoding RNA in Cancer Stem Cells Maintains ICAM-1 Expression in Hepatocellular Carcinoma." Clin Cancer Res, Apr. 15, 2016, 22(8): 2041-2050.
Lumsden, A.L., et al., "ICAM-1-related long non-coding RNA: promoter analysis and expression in human retinal endothelial cells." BMC Res Notes, 2018, 11(285): 1-8.
Perry, M.M., et al., "Role of non-coding RNAs in maintaining primary airway smooth muscle cells." Respiratory Research, 2014, 15(58): 1-12.
Persson, H., et al., "Transcriptome analysis of controlled and therapy-resistant .childhood asthma reveals distinct gene expression profiles." J Allergy Clin Immunol, Sep. 2015, 136(3): 638-648.
Tsitsiou, E., et al., "Transcriptome analysis shows activation of circulating CD81 T cells in patients with severe asthma." J Allergy Clin Immunol, Jan. 2012, 129(1): 95-103.
Wang, S.Y., et al., "The lncRNAs involved in mouse airway allergic inflammation following induced pluripotent stem cell-mesenchymal stem cell treatment." Stem Cell Research & Therapy, 2017, 8(2): 1-14.

(Continued)

*Primary Examiner* — Brian Whiteman

(74) *Attorney, Agent, or Firm* — Saliwanchik, Lloyd & Eisenschenk

(57) ABSTRACT

The subject invention provides methods, assays, and products for preventing and/or treating pulmonary diseases. The present invention provides methods for identifying inhibitors of lncRNAs, pharmaceutical compositions comprising such inhibitors, and method of using said inhibitors in preventing and/or treating pulmonary airway inflammation. The present invention also develop novel strategies to modulate the mucous response for preventing, intervening, diagnosing and treating pulmonary airway inflammation, asthma, chronic obstructive pulmonary diseases (COPD) and Chronic mucus hypersecretion (CMH) pathogenesis.

20 Claims, 9 Drawing Sheets

Specification includes a Sequence Listing.

(56) References Cited

OTHER PUBLICATIONS

Yu, X., et al., "α-Asarone suppresses the proliferation and migration of ASMCs through targeting the lncRNA-PVT1/miR-203a/E2F3 signal pathway in RSV-infected rats." Acta Biochim Biophys Sin, 2017, 49(7): 598-608.
Zhang, X.Y., et al., "LncRNAs BCYRN1 promoted the proliferation and migration of rat airway smooth muscle cells in asthma via upregulating the expression of transient receptor potential 1." Am J Transl Res, 2016, 8(8): 3409-3418.
Zhang, X.Y., et al., "Schisandrin B down-regulated lncRNA BCYRN1 expression of airway smooth muscle cells by improving miR-150 expression to inhibit the proliferation and migration of ASMC in asthmatic rats." Cell Proliferation, 2017, 50: e12382, 1-7.
Zhu, Y.J., et al., "Peripheral whole blood lncRNA expression analysis in patients with eosinophilic asthma." Medicine, 2018, 97(8): 1-9.

\* cited by examiner

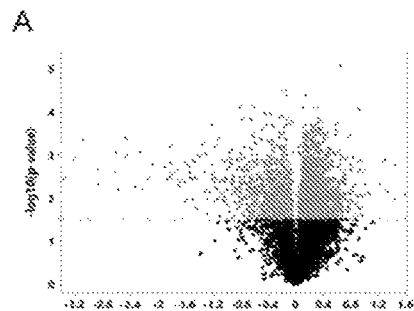
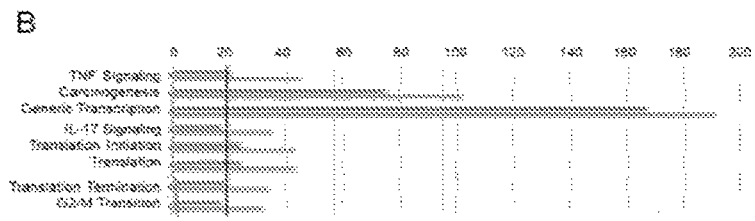
FIG. 2A  FIG. 2B
FIG. 3A  FIG. 3B
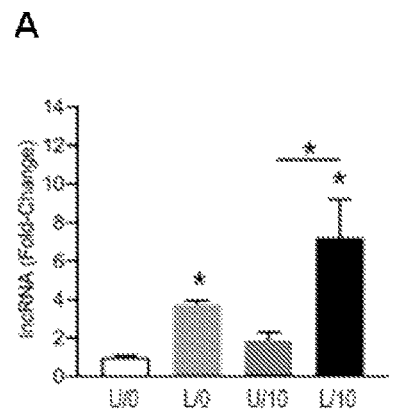
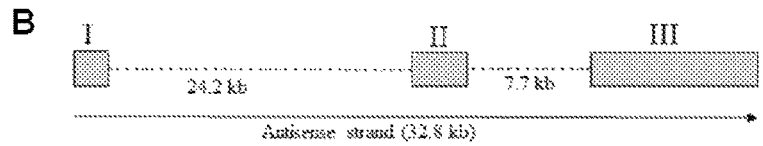
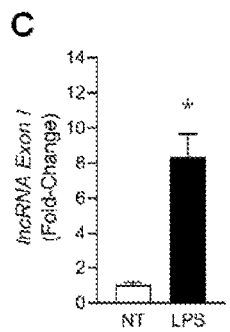
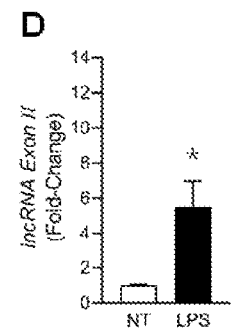
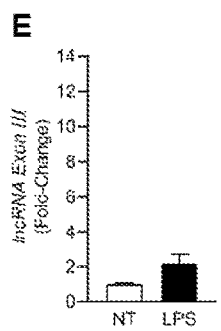
FIG. 3C  FIG. 3D  FIG. 3E

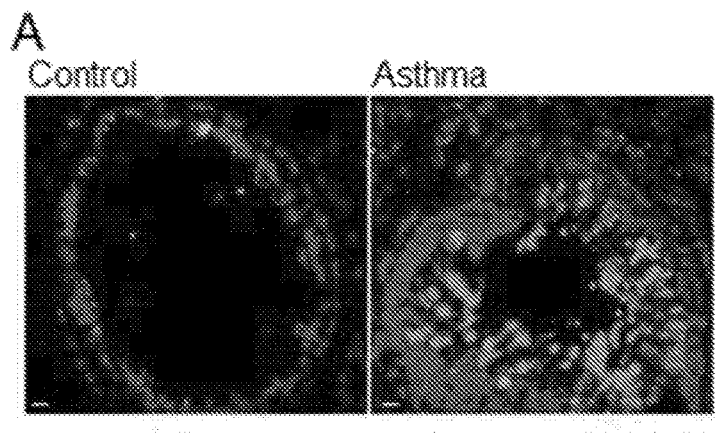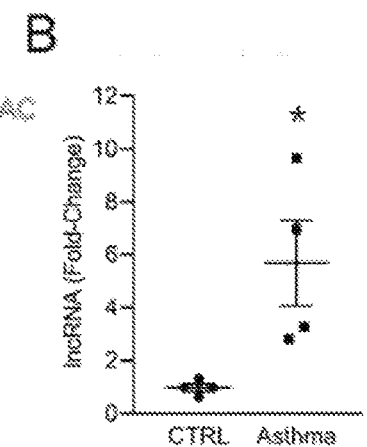
FIG. 4A    FIG. 4B
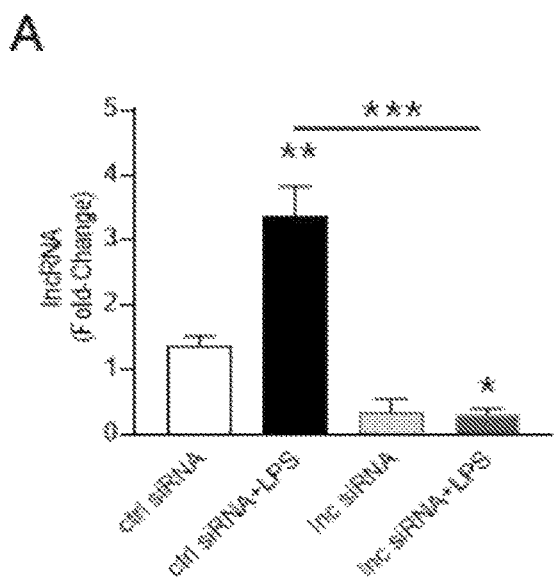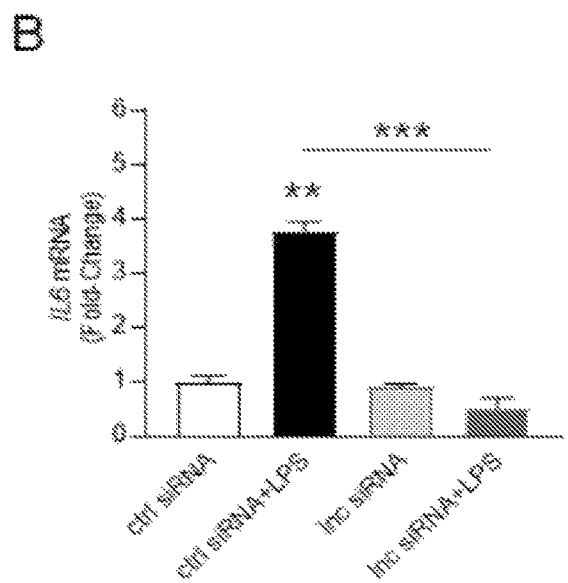
FIG. 5A    FIG. 5B

A

B

A.
|  | CTRL (n=6) | COPD (n=5) |
|---|---|---|
| Age* | 56.3 ± 12.4 | 53.7 ± 2.1 |
| Gender, M/F | 3/3 | 4/1 |
| Smoking in PY* | 23.9 ± 11.6 | 41.9 ± 21.8 |
| Stop Smoking (Y)* | 9.6 ± 6.1 | 8.2 ± 5.3 |
* Mean ± SD; M = male; F = female; PY = Packs per Year; Y = years
FIG. 9A
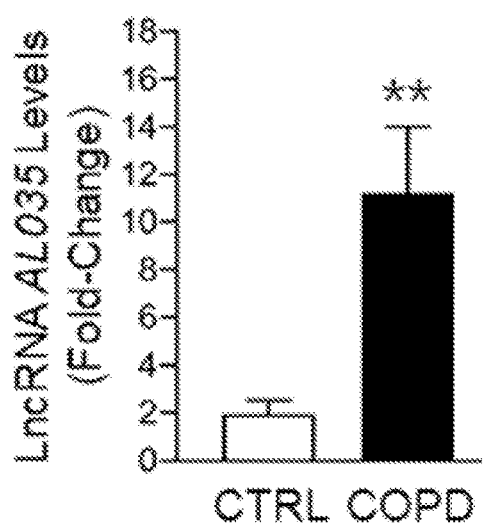
FIG. 9B
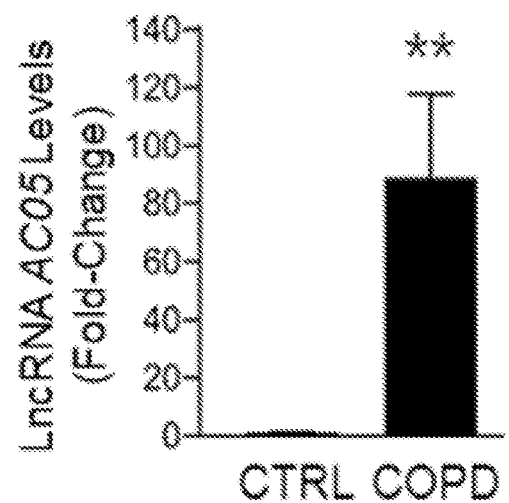
FIG. 9C

LONG NONCODING RNAS IN PULMONARY AIRWAY INFLAMMATION

CROSS-REFERENCE TO A RELATED APPLICATION

This application claims the benefit of U.S. provisional application Ser. No. 62/785,887, filed Dec. 28, 2018, which is incorporated herein by reference in its entirety.

GOVERNMENT SUPPORT

This invention was made with government support under AI117560 awarded by the National Institutes of Health. The government has certain rights in the invention.

SEQUENCE LISTING

The Sequence Listing for this application is labeled "SeqList-06Mar20_ST25.txt," which was created on Mar. 6, 2020, and is 12 KB. The Sequence Listing is incorporated herein by reference in its entirety.

BACKGROUND OF THE INVENTION

Chronic mucus hypersecretion (CMH) is a global healthcare problem that particularly affects asthmatics, including over 24.6 million in the USA with conservative estimates of annual healthcare costs exceeding 56 billion dollars. Allergic asthmatics suffer from hyperreactive mucous responses that block the airways and affect the lung function, resulting in associated morbidities and mortalities. Chronic bronchitis (CB) or chronic mucus hypersecretion (CMH) results from mucus overproduction by goblet cells, leading to airway obstruction and decline in lung function. COPD encompasses a spectrum of diseases including CB, reduced lung function, and emphysema and its severity is linked to CMH.

Smoking is a paramount risk factor for CMH that leads to decline in lung function and lung diseases such as CB, COPD, and asthma. Cigarette smoke contains an extremely high concentration of oxidants. The reactive oxidant substances generated by smoking induce inflammation in the lung and its airway, e.g., the central airways, peripheral airways, and lung parenchyma. Although smoking is the most common risk factor for COPD, other risk factors such as air pollution, e.g., from the burning of wood and other biomass fuels, and passive exposure to cigarette smoke may also contribute to the development of COPD by increasing the total burden of the lungs.

Inhalational exposures to environmental toxicants, airborne pathogens and microbial byproducts shape the pulmonary immune responses. Endotoxins are bacterial cell wall components ubiquitously present in dust and ambient air. Several cross-sectional and longitudinal studies suggest that exposures to endotoxin affect the onset and progression of asthma. The effects of endotoxin exposure in terms of time, duration, dose, and atopy are influenced by the variants in endotoxin responsive genes.

Although the memory-based acquired immune responses play a pivotal role, the immunologic memory developed by innate immune cells have also been shown to contribute to the host-beneficial "trained" responses. Such trained response can be developed through repetitive exposures or so-called "experiments of nature" in several immune cells resulting from genetic and epigenetic remodeling.

Airway epithelial cells (AECs) preserve a near-sterile microenvironment via mucociliary clearance mechanisms and more importantly, by an adaptive mucosal immune response. The conducting airway epithelium consists of basal, ciliated, club (or Clara) and mucous (or goblet) cells. The most abundant mucins secreted by airway epithelial cells (AECs) are MUC5AC and MUC5B, which, in combination with other proteins, lipids and glycosylated factors, form a mucous layer. The airway surface mucous layer not only serves as a barrier but also traps inhaled particles for mucociliary clearance.

The airway epithelium has evolved several regulatory mechanisms to control hyperreactive inflammatory responses to minimize deleterious effects. Lymphocytes, monocytes, macrophages, and dendritic cells possess 'dynamic cellular programing' or 'memory' to adjust the immune response to secondary challenges.

The airway epithelium in asthmatics is in a state of altered epithelial homeostasis resulting in a 'trained' mucous response. Recurring exposures to microbial ligands have been shown to propagate a memory-based response in monocytes, macrophages and NK cells; however, contribution of the AECs in this trained response is not known.

Recent large-scale RNA profiling efforts have revealed that >75% of the human genome is transcribed and only <2% of human genome is translated into proteins. Thus, the human genome produces a large number of noncoding RNAs (ncRNAs) including housekeeping or "classic" ncRNAs, small ncRNAs, and long noncoding RNAs (lncRNAs). Housekeeping ncRNAs include ribosomal RNAs (rRNAs), transfer RNAs (tRNAs), small nuclear RNAs (snRNAs), and small nucleolar RNAs (snoRNAs). Small ncRNAs include microRNAs (miRNAs), endogenous small interfering (endo-si)RNAs, PIWI-associated RNAs (piRNAs), and promoter associated RNAs (paRNAs). LncRNAs include long intergenic ncRNAs (lincRNAs), natural antisense transcripts (NATs), intronic lncRNAs, pseudogenic transcripts, circular RNAs (circRNAs), long enhancer ncRNAs, transcribed ultraconserved regions (T-UCRs).

LncRNAs are a major part of the human transcriptome and are defined as the autonomously transcribed RNA longer than 200 nucleotides. According to their location in the genome, lncRNAs are categorized into four groups: intronic, exonic, overlapping and intergenic.

Biological functions of lncRNAs attribute to protein activity modulation, protein localization, chromatin modification, transcription initiation/repression, alternative splicing, and mRNA decay. However, only a small fraction of the large set of lncRNAs has been characterized. While a large number of miRNAs have been identified and characterized for their role in epithelial cell functions and airway remodeling, the regulation and function of lncRNAs in airway epithelium is poorly understood.

Therefore, there is a need to identify novel lncRNAs, in particular, those involved in the regulation of airway inflammation and remodeling. There are also needs to develop novel strategies to modulate the mucous response and to develop methods and compositions for preventing, intervening, diagnosing and treating pulmonary airway inflammation, asthma, chronic obstructive pulmonary diseases (COPD) and CMH pathogenesis, for example, through attenuating mucus hyperreactivity and exacerbations.

BRIEF SUMMARY OF THE INVENTION

The subject invention provides methods, assays, and products for detecting, monitoring, preventing and/or treating pulmonary diseases. For example, the present invention provides methods for identifying inhibitors of lncRNAs, pharmaceutical compositions comprising such inhibitors, and methods of using said inhibitors in preventing and/or treating pulmonary airway inflammation.

In one embodiment, the lncRNAs include lncRNA AL357060.1 (ENSG00000237499), AC011511.2 (ENSG00000266978) and AC007389.1 (ENSG00000204929). AL357060.1 lncRNA has 4 exons and is on the antisense strand of the gene encoding TNF alpha induced protein 3 (TNFAIP3). AC011511.2 lncRNA comprises 3 exons and overlaps with intracellular adhesion molecule 1 (ICAM-1) on the antisense strand and regulates ICAM-1 expression. AC007389.1 lncRNA is encoded by a 650 kb gene with 10 exons.

In one embodiment, the present invention provides inhibitors of lncRNAs. Preferably, the inhibitors target the exon regions of the lncRNAs. The inhibitors of lncRNAs can be short, chemically-engineered single-stranded oligonucleotides complementary to lncRNAs that block the function of lncRNAs. Preferably, the inhibitors of lncRNAs are small interfering RNAs (siRNAs).

In specific embodiments, the inhibitor of lncRNAs comprises, or consists of, an oligonucleotide selected from (i) an antisense oligonucleotide to the nucleotide sequence of a lncRNA selected from AL357060.1, AC011511.2 and AC007389.1; and (ii) a nucleic acid sequence that is complementary to at least 10, 15, 20, 25, 30, 35, 40, 45, 50, 55, 60, 65, 70, 75, 80, 85, 90, 95, 100 contiguous nucleotides of the nucleotide sequence of a lncRNA selected from AL357060.1, AC011511.2 and AC007389.1.

The present invention provides pharmaceutical composition comprising at least one inhibitor of a lncRNA according to the invention, optionally, a pharmaceutical excipient, and optionally, a further pulmonary medicament.

The present invention also provides a pharmaceutical compositions comprising at least one modulator/inhibitor of a lncRNA selected from lncRNA AL357060.1, AC011511.2 and AC007389.1 in a form that can be combined with a pharmaceutically acceptable carrier.

In one embodiment, the compositions of the present invention can be used to treat, alleviate, or ameliorate allergic responses. This can include the use of the modulator of lncRNAs for the treatment of acute allergic reactions such as acute asthmatic attack and in the treatment of inflammation of the lung caused by chemical exposure.

In one embodiment, the subject invention provides a method for detecting, monitoring and/or treating pulmonary airway inflammation in a subject. The method for the treatment comprising administering a pharmaceutical composition to the subject to treat and/or manage the pulmonary airway inflammation, the subject having been determined to have increased level in at least one lncRNA. Such determination comprises (a) determining the level of at least one lncRNA in: i) a test sample obtained from the subject, and ii) optionally, a control sample; (b) optionally, obtaining at least one reference value corresponding to the level of at least one lncRNA; and (c) identifying the pulmonary airway inflammation in the subject based on the levels of at least one lncRNAs in the test sample.

Various techniques are well known to a person of ordinary skill in the art to determine the level of lncRNAs in a sample. Non-limiting examples of such techniques include microarray analysis, real-time polymerase chain reaction (PCR), Northern blot, in situ hybridization, solution hybridization, and quantitative reverse transcription PCR (qRT-PCR). Methods for carrying out these techniques are routine in the art.

In certain embodiments, the control sample and the test sample are obtained from the same type of body fluid. Non-limiting examples of the body fluids that can be used as samples include, urine, aqueous humor, vitreous humor, bile, blood, cerebrospinal fluid, chyle, endolymph, perilymph, lymph, mucus (including nasal drainage and phlegm), pericardial fluid, peritoneal fluid, pleural fluid, pus, rheum, saliva, sputum, synovial fluid, vaginal secretion, blood, serum or plasma. Additional examples of body fluids are well known to a person of ordinary skill in the art and such embodiments are within the purview of the invention.

BRIEF DESCRIPTION OF THE DRAWINGS

FIGS. 2A-2B show the transcriptomic analysis of immediate early innate responses of human AECs. Primary human AECs were differentiated at the air-liquid interface (ALI) and were treated with LPS (100 ng/ml) for 2 h. Total RNA was isolated from cells and RNAseq analysis was performed. (2A) Volcano plot of 3,164 significantly expressed genes following LPS challenge of human AECs. (2B) ToppFun pathway analysis demonstrates upregulation of proinflammatory response and cytokine signaling.

FIGS. 3A-3E show LPS induced expression of lncRNA AC011511.2 in human AECs showing hyperreactive mucous response. (3A) Relative quantities of lncRNA levels in U/0, L/0, U/10, and L/10 human AECs as determined by qRT-PCR. (3B) Human lncRNA AC011511.2 gene annotation showing exon I, II and III. Relative quantities of lncRNA AC011511.2 exon I (3C), exon II (3D) and exon III (3E) mRNA levels in LPS treated human AECs compared to non-treated (NT) controls. (n=3; *p<0.05).

FIGS. 4A-4B show the upregulated mucous and lncRNA AC011511.2 levels in asthmatic airways. (4A) airway sections stained with MUC5AC (green) and DAPI-stained nuclei (blue) from control and asthma subjects. (4B) Relative quantity of lncRNA AC011511.2 in asthma AECs compared to controls. scale—5µ.

FIGS. 5A-5D show that knocking down lncRNA AC011511.2 in AECs suppresses the LPS-induced inflammatory responses. Relative quantities of AC011511.2 lncRNA (5A), IL-6 (5B), ICAM-1 (5C) and CXCL-8 (5D) mRNA levels in LPS treated human AECs that were transfected with siRNA targeting AC011511.2 lncRNA compared to control siRNA transfected cells.

FIGS. 9A-9F show elevated levels of LncRNA AL35 and AC05 in former smoker COPD subjects with the expression localized in the cytosolic region of airway epithelial cells. (9A) Demographics of the former smokers with and without COPD analyzed in this study. Relative quantities of lncRNA AL357060.1 (AL35) (9B) and lncRNA AC011511.2 (AC05) (9C) transcript levels in former smoker COPD subjects compared to non-COPD former smoker controls (CTRL); **p<0.01. (9D) Representative bronchial airway sections from COPD subjects showing AC05 (red) transcript levels in airway epithelial cells compared to the control tissue. DAPI-stained nuclei are shown in blue, scale—5µ. (9E) Quantification of AC05 transcript levels per epithelial cell of control and COPD subjects (n=3). (9F) Relative distribution of ACOS transcript levels in the nuclear and the cytosolic region of the analyzed subjects.

BRIEF DESCRIPTION OF SEQUENCES

Figure 1A:
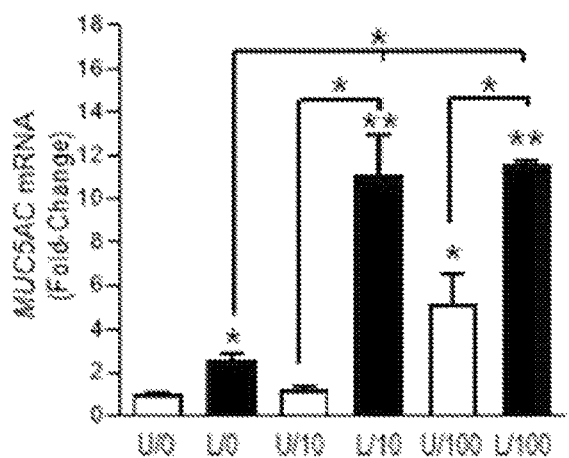
FIGS. 1A-1D show the trained mucous response in differentiated human AECs following lipopolysaccharide (LPS) challenge. Differentiated human AECs were treated with 100 ng/ml LPS (L) or were left untreated (U), and then on d 10 were challenged with LPS at 0, 10 or 100 ng/ml. Groups were identified as U/0, U/10 and U/100 or L/0, L/10 and L/100, respectively. Relative quantities of MUC5AC (1A) and SPDEF (1B) mRNA levels in U/0, L/0, U/10, L/10, U/100 and L/100 human AECs as determined by qRT-PCR. (1C) Micrographs of differentiated human AECs stained for beta-tubulin (green, ciliated cells) and MUC5AC (red); and DAPI-stained nuclei (blue) from U/0, L/0, U/10 and L/10 human AECs. (1D) Quantification of MUC5AC+human AECs. Scale—5µ.

SEQ ID NOs: 1-3 are nucleic acid sequences of exons of lncRNA AC011511.2 contemplated for use according to the subject invention.

SEQ ID NO: 4 is the sense stand of X1 siRNA (6-30) contemplated for use according to the subject invention.

SEQ ID NO: 5 is the antisense stand of X1 siRNA (6-30) contemplated for use according to the subject invention.

SEQ ID NO: 6 is the sense stand of X2-A siRNA (26-50) contemplated for use according to the subject invention.

SEQ ID NO: 7 is the antisense stand of X2-A siRNA (26-50) contemplated for use according to the subject invention.

SEQ ID NO: 8 is the sense stand of X2-B siRNA (35-59) contemplated for use according to the subject invention.

SEQ ID NO: 9 is the antisense stand of X2-B siRNA (35-59) contemplated for use according to the subject invention.

SEQ ID NO: 10 is the sense stand of X3 siRNA (37-61) contemplated for use according to the subject invention.

SEQ ID NO: 11 is the antisense stand of X3 siRNA (37-61) contemplated for use according to the subject invention.

SEQ ID NOs: 12 and 14 are forward primers contemplated for use according to the subject invention.

SEQ ID NOs: 13 and 15 are reverse primers contemplated for use according to the subject invention.

SEQ ID NO: 16 is the target sequence of X1 siRNA (6-30) contemplated for use according to the subject invention.

SEQ ID NO: 17 is the target sequence of X2-A siRNA (26-50) contemplated for use according to the subject invention.

SEQ ID NO: 18 is the target sequence of X2-B siRNA (35-59) contemplated for use according to the subject invention.

SEQ ID NO: 19 is the target sequence of X3 siRNA (37-61) contemplated for use according to the subject invention.

SEQ ID NO: 20 is the target sequences of lncRNA-X1 contemplated for use according to the subject invention.

SEQ ID NO: 21 is the target sequences of lncRNA-X2 contemplated for use according to the subject invention.

SEQ ID NO: 22 is the target sequences of lncRNA-X3 contemplated for use according to the subject invention.

SEQ ID NO: 23 is a nucleic acid sequence of lncRNA AL357060.1 contemplated for use according to the subject invention.

SEQ ID NOs: 24-27 are nucleic acid sequences of exons of lncRNA AL357060.1 contemplated for use according to the subject invention.

SEQ ID NO: 28 is a forward primer for exon 3 of lncRNA AL357060.1 contemplated for use according to the subject invention.

SEQ ID NO: 29 is a probe sequence for exon 3 of lncRNA AL357060.1 contemplated for use according to the subject invention.

SEQ ID NO: 30 is a reverse primer for exon 3 of lncRNA AL357060.1 contemplated for use according to the subject invention.

SEQ ID NO: 31 is a forward primer for exon 4 of lncRNA AL357060.1 contemplated for use according to the subject invention.

SEQ ID NO: 32 is a probe sequence for exon 4 of lncRNA AL357060.1 contemplated for use according to the subject invention.

SEQ ID NO: 33 is a reverse primer for exon 4 of lncRNA AL357060.1 contemplated for use according to the subject invention.

DETAILED DESCRIPTION OF THE INVENTION

The present invention relates to the identification of lncRNAs that are involved in the pathogenesis of chronic pulmonary diseases. The present invention further relates to the identification of inhibitors of lncRNAs, pharmaceutical compositions comprising such inhibitors, and their use in preventing and/or treating chronic pulmonary diseases. The present invention further relates to lncRNAs for use in the diagnosis, prognosis, prevention and/or treatment of a chronic pulmonary disease.

LncRNA

"Long non-coding RNAs" or "lncRNAs" as used herein refers to transcribed RNA molecules having a length of greater than 200 nucleotides that do not encode proteins, mRNA, rRNA, or tRNA. lncRNAs for use in the instant invention include those lncRNAs that play roles in cell survival, inflammation, and gene expression. LncRNAs include long intergenic ncRNAs (lincRNAs), natural antisense transcripts (NATs), intronic lncRNAs, pseudogenic transcripts, circular RNAs (circRNAs), long enhancer ncRNAs, transcribed ultraconserved regions (T-UCRs).

In one embodiment, the lncRNAs, mimics and/or fragments thereof according to the present invention comprise a nucleotide sequence longer than 200 nucleotides, 250 nucleotides, 300 nucleotides, 350 nucleotides, 400 nucleotides, 450 nucleotides, 500 nucleotides, 550 nucleotides, 600 nucleotides, 650 nucleotides, 700 nucleotides, 750 nucleotides, 800 nucleotides, 850 nucleotides, 900 nucleotides, 950 nucleotides, or 1000 nucleotides.

In other embodiments, the lncRNAs, mimics and/or fragments thereof according to the present invention comprise a nucleotide sequence having a length from about 200 nucleotides to about 10,000 nucleotides, from about 200 nucleotides to about 9500 nucleotides, from about 200 nucleotides to about 9000 nucleotides, from about 200 nucleotides to about 8500 nucleotides, from about 200 nucleotides to about 8000 nucleotides, from about 200 nucleotides to about 7500 nucleotides, from about 200 nucleotides to about 7000 nucleotides, from about 200 nucleotides to about 6500 nucleotides, from about 200 nucleotides to about 6000 nucleotides, from about 200 nucleotides to about 5500 nucleotides, from about 200 nucleotides to about 5000 nucleotides, from about 300 nucleotides to about 5000 nucleotides, from about 400 nucleotides to about 5000 nucleotides, from about 500 nucleotides to about 5000 nucleotides, from about 600 nucleotides to about 5000 nucleotides, from about 700 nucleotides to about 5000 nucleotides, from about 800 nucleotides to about 4500 nucleotides, from about 900 nucleotides to about 4000 nucleotides, from about 1000 nucleotides to about 3500 nucleotides, from about 1000 nucleotides to about 3000 nucleotides, from about 1100 nucleotides to about 3000 nucleotides, from about 1200 nucleotides to about 2500 nucleotides, from about 1500 nucleotides to about 2000 nucleotides, from about 1000 nucleotides to about 1500 nucleotides, from about 500 nucleotides to about 2000 nucleotides, or from about 200 nucleotides to about 1500 nucleotides.

In one embodiment, the lncRNA mimics may include, but are not limited to, nucleic acid mimics having nucleobases bound to backbones other than the naturally occurring ribonucleic acid or deoxyribonucleic acid backbones and having the ability to bind to nucleic acids having a nucleobase sequence complementary to the base sequence of the nucleic acid mimic. The lncRNA mimics exhibit identical or similar activities and functions of lncRNAs. In a specific embodiment, the lncRNA mimics may be peptide nucleic acids (PNAs).

In one embodiment, the lncRNAs include, but are not limited to lncRNA AL357060.1 (ENSG00000237499), AC011511.2 (ENSG00000266978) and AC007389.1 (ENSG00000204929). AL357060.1 lncRNA has 4 exons and is on the antisense strand of the gene encoding TNF alpha induced protein 3 (TNFAIP3). AC011511.2 lncRNA comprises 3 exons and overlaps with intracellular adhesion molecule 1 (ICAM-1) on the antisense strand and regulates ICAM-1 expression. AC007389.1 lncRNA is encoded by a 650 kb gene with 10 exons.

In a specific embodiment, lncRNA locates on the opposite strand to ICAM-1 and MRPL4 at chromosome 19.

In one embodiment, the genes and/or lncRNAs of the present invention may serve as biomarkers for: (1) the diagnosis of disease; (2) the prognosis of disease (e.g. monitoring disease progression or regression from one biological state to another); (3) the susceptibility or prediction of response to treatment for a disease; and/or (4) the evaluation of the efficacy to a treatment for disease.

For the diagnosis of disease, the level of the specific lncRNA in a subject or a sample of the subject can be compared to a baseline or control level. If the level is below the control level, a certain disease is implicated. The prognosis of disease can be assessed by comparing the level of the specific biomarker at a first time point to the level of the biomarker at a second time point that occurs at a given interval. The prediction of response to treatment for a disease can be determined by obtaining the level of a specific lncRNA biomarker and correlating this level to a standard curve. The evaluation of the efficacy of the treatment for a disease can be assessed by comparing the level of the specific biomarker before administration of the treatment to the level of the biomarker after the administration of the treatment.

Expression of genes/transcripts of the present invention can be measured by many methods known in the art. In general, expression of a nucleic acid molecule (e.g. RNA or DNA) can be detected by any suitable method or technique of measuring or detecting gene or polynucleotide sequence or expression. Such methods include, but are not limited to, polymerase chain reaction (PCR), reverse transcriptase PCR (RT-PCR), in situ PCR, quantitative PCR (q-PCR), in situ hybridization, Southern blot, Northern blot, sequence analysis, microarray analysis, detection of a reporter gene, or any other DNA/RNA hybridization platforms.

Inhibitor of lncRNA

In one embodiment, the present invention provides inhibitors of lncRNAs selected from AL357060.1, AC011511.2 and AC007389.1. Preferably, the inhibitors target the exon regions of the lncRNAs. The inhibitors of lncRNAs can be short, chemically-engineered single-stranded oligonucleotides complementary to lncRNAs that block the function of lncRNAs. Preferably, the inhibitors of lncRNAs are small interfering RNAs (siRNAs).

In specific embodiments, the inhibitor of lncRNAs comprises, or consists of, an oligonucleotide selected from (i) an antisense oligonucleotide to the nucleotide sequence of a lncRNA selected from AL357060.1, AC011511.2 and AC007389.1; and (ii) a nucleic acid sequence that is complementary to at least 10, 15, 20, 25, 30, 35, 40, 45, 50, 55, 60, 65, 70, 75, 80, 85, 90, 95, 100 contiguous nucleotides of the nucleotide sequence of a lncRNA selected from AL357060.1, AC011511.2 and AC007389.1.

In preferred embodiments, the inhibitor of lncRNAs comprises, or consists of, an oligonucleotide selected from (i) an antisense oligonucleotide to the nucleotide sequence of one of the exons of lncRNA selected from AL357060.1, AC011511.2 and AC007389.1; and (ii) a nucleic acid sequence that is complementary to at least 10, 15, 20, 25, 30, 35, 40, 45, 50, 55, 60, 65, 70, 75, 80, 85, 90, 95, 100 contiguous nucleotides of the nucleotide sequence of one of the exons of lncRNA selected from AL357060.1, AC011511.2 and AC007389.1.

The oligonucleotide can also comprise a nucleic acid sequence that is complementary to a sequence having at least 80%, 85%, 90%, 95%, 98%, or 99% sequence identity to a nucleotide sequence of a lncRNA selected from AL357060.1, AC011511.2 and AC007389.1, or a nucleotide sequence of one of the exons of a lncRNA selected from AL357060.1, AC011511.2 and AC007389.1.

In one embodiment, the oligonucleotide sequence is about 10 to about 100 nucleotides in length, such as about 10 to about 90, about 10 to about 80, about 10 to about 70, about 10 to about 60, about 10 to about 50, about 10 to about 40, about 10 to about 30, or about 20 to about 30.

In one embodiment, the oligonucleotide sequence targets exon 1 (SEQ ID NO: 1), exon 2 (SEQ ID NO: 2), or exon 3 (SEQ ID NO: 3) of lncRNA AC011511.2. The oligonucleotide sequence can also target exon 1 (SEQ ID NO: 24), exon 2 (SEQ ID NO: 25), exon 3 (SEQ ID NO: 26), or exon 4 (SEQ ID NO: 27) of AL357060.1. The oligonucleotide sequence can also target exon 1, exon 2, exon 3, exon 4, exon 5, exon 6, exon 7, exon 8, exon 9 or exon 10 of AC007389.1.

In one embodiment, the oligonucleotide sequence is complementary to at least 10 contiguous nucleotides of the nucleotide sequence selected from exon 1, exon 2, and exon 3 of AC011511.2; exon 1, exon 2, exon 3, and exon 4 of AL357060.1; or exon 1, exon 2, exon 3, exon 4, exon 5, exon 6, exon 7, exon 8, exon 9 and exon 10 of AC007389.1.

In specific embodiments, the oligonucleotide sequence targets or is complementary to oligonucleotide position 6-30 of exon 1 of lncRNA AC011511.2 (SEQ ID NO: 16), position 26-50 of exon 2 of lncRNA AC011511.2 (SEQ ID NO: 17), position 35-59 of exon 2 of lncRNA AC011511.2 (SEQ ID NO: 18), or position 37-61 of exon 3 of lncRNA AC011511.2 (SEQ ID NO: 19). Also, the oligonucleotide sequence may comprise an antisense oligonucleotide to the nucleotide sequence of position 6-31 (SEQ ID NO: 16) of exon 1 of lncRNA AC011511.2, position 26-51 (SEQ ID NO: 17) of exon 2 of lncRNA AC011511.2, position 35-60 (SEQ ID NO: 18) of exon 2 of lncRNA AC011511.2, or position 37-62 (SEQ ID NO: 19) of exon 3 of lncRNA AC011511.2.

In certain embodiment, the inhibitor of lncRNAs comprises, or consists of, one or more oligonucleotides selected from
(i) an antisense oligonucleotide to the nucleotide sequence of position 6-30 of exon 1 of lncRNA AC011511.2 (SEQ ID NO: 16), position 26-50 of exon 2 of lncRNA AC011511.2 (SEQ ID NO: 17), position 35-59 of exon 2 of lncRNA AC011511.2 (SEQ ID NO: 18), or position 37-61 of exon 3 of lncRNA AC011511.2 (SEQ ID NO: 19); and
(ii) a nucleic acid sequence that is complementary to position 6-31 of exon 1 of lncRNA AC011511.2 (SEQ ID NO: 16), position 26-51 of exon 2 of lncRNA AC011511.2 (SEQ ID NO: 17), position 35-60 of exon 2 of lncRNA AC011511.2 (SEQ ID NO: 18), or position 37-62 of exon 3 of lncRNA AC011511.2 (SEQ ID NO: 19).

In a preferred embodiment, the inhibitor of lncRNAs comprises a siRNA targeting exon 1 (SEQ ID NO: 1), exon 2 (SEQ ID NO: 2), or exon 3 (SEQ ID NO: 3) of lncRNA AC011511.2. The siRNA is selected from

```
(a) X1siRNA (6-30):
                                    (SEQ ID NO: 4)
5'-AUACAACAGGCGGUGAGGAUUGC

AT-3'
(sense strand)

(SEQ ID NO: 5)
5'-AUGCAAUCCUCACCGCCUGUUGU

AUCC-3';
(antisense strand)

(b) X2-A siRNA (26-50):
                                    (SEQ ID NO: 6)
5'-ACACAACAUCUACUUGUACAAUC

AA-3'
(sense strand)

(SEQ ID NO: 7)
5'-UUGAUUGUACAAGUAGAUGUUGU

GUAA-3';
(antisense strand)

(c) X2-B siRNA (35-59):
                                    (SEQ ID NO: 8)
5'-CUACUUGUACAAUCAAGCACACA

CT-3'
(sense strand)

(SEQ ID NO: 9)
5'-AGUGUGUGCUUGAUUGUACAAGU
```

```
                    -continued
AGAU-3';
(antisense strand)
and (d) X3 siRNA (37-61):
                                    (SEQ ID NO: 10)
5'-CCAAGGGUACAAGCCCAAAGUCA TC-3'
(sense strand)

(SEQ ID NO: 11)
5'-GAUGACUUUGGGCUUGUACCCUU

GGGA-3'.
(antisense strand)
```

In a specific embodiment, the inhibitor of lncRNAs is selected from X1 siRNA (6-30), X2-A siRNA (26-55), X2-B siRNA (35-59), and X3 siRNA (37-61).

In some embodiments, the inhibitor of lncRNAs comprises, or consists of, one or more oligonucleotides selected from
(i) an antisense oligonucleotide to the nucleotide sequence of exon 1 (SEQ ID NO: 24), exon 2 (SEQ ID NO: 25), exon 3 (SEQ ID NO: 26), exon 4 (SEQ ID NO: 27) of AL357060.1, and/or fragments thereof; and
(ii) a nucleic acid sequence that is complementary to the nucleotide sequence of exon 1 (SEQ ID NO: 24), exon 2 (SEQ ID NO: 25), exon 3 (SEQ ID NO: 26), exon 4 (SEQ ID NO: 27) of AL357060.1, and/or fragments thereof.

In a preferred embodiment, the inhibitor of lncRNAs comprises a siRNA targeting the nucleotide sequence of exon 1 (SEQ ID NO: 24), exon 2 (SEQ ID NO: 25), exon 3 (SEQ ID NO: 26), exon 4 (SEQ ID NO: 27) of AL357060.1, and/or fragments thereof.

In one embodiment, the inhibitor of lncRNAs comprises an oligonucleotide sequence complementary to at least 20 contiguous nucleotides of the nucleotide sequence selected from exon 1 of AL357060.1, exon 2 of AL357060.1, exon 3 of AL357060.1, exon 4 of AL357060.1, exon 1 of AC007389.1, exon 2 of AC007389.1, exon 3 of AC007389.1, exon 4 of AC007389.1, exon 5 of AC007389.1, exon 6 of AC007389.1, exon 7 of AC007389.1, exon 8 of AC007389.1, exon 9 of AC007389.1 and exon 10 of AC007389.1.

In some embodiments, the oligonucleotide may be modified or conjugated near or at an end, such as near or at the 3' end or 5' end, preferably with hydrophobic group(s) or moiety(ies), such as cholesterol.

The oligonucleotide/antisense oligonucleotide/siRNA of the present invention may or may not include chemical modifications as described herein such as a chemical substitution at a sugar position, a phosphate position, and/or a base position of the nucleic acid including, for example, incorporation of a modified nucleotide, incorporation of a capping moiety (e.g., 3' capping), conjugation to a high molecular weight, non-immunogenic compound (e.g., polyethylene glycol (PEG)), conjugation to a lipophilic compound, and substitutions in the phosphate backbone. In some embodiments, each base of a given type (e.g., A, U, C, and G) may contain the same chemical modification.

Pharmaceutical Compositions

The present invention provides a pharmaceutical composition comprising at least one inhibitor of a lncRNA according to the invention, optionally, a pharmaceutical excipient, and optionally, a further pulmonary medicament.

The present invention also provides a pharmaceutical compositions comprising at least one modulator/inhibitor of a lncRNA selected from lncRNA AL357060.1, AC011511.2 and AC007389.1 in a form that can be combined with a pharmaceutically acceptable carrier.

The term "carrier" refers to a diluent, adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The therapeutic composition, if desired, can also contain minor amounts of wetting or emulsifying agents, or pH buffering agents. These compositions can take the form of solutions, suspensions, emulsion, tablets, capsules, powders, sustained-release formulations and the like. The composition can be formulated with traditional binders and carriers such as triglycerides. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the patient. The formulation should suit the mode of administration.

The pharmaceutical compositions of the present invention are useful to treat or ameliorate diseases, including pulmonary disorders including diseases such as asthma and asthma-associated diseases (e.g., exercise-induced asthma, rhinitis, chronic obstructive pulmonary disease, interstitial lung disease, chronic urticaria, atopic dermatitis, allergic fungal diseases, nasal polyposis, and paranasal sinus disease); chronic bronchitis, and related obstructive airway diseases such as COPD; allergies and allergic reactions such as allergic rhinitis, contact dermatitis, allergic conjunctivitis, and the like; chronic lung diseases such as cystic fibrosis, bronchitis and other small and large-airway diseases; and cholecystitis.

The composition of the present invention comprises at least one modulator/inhibitor of lncRNAs and optionally one or more further active agents. The additional active agents may include, for example:

1) steroid drugs such as, for example, alcometasone, beclomethasone, beclomethasone dipropionate, betamethasone, budesonide, clobetasol, deflazacort, diflucortolone, desoxymethasone, dexamethasone, fludrocortisone, flunisolide, fluocinolone, fluometholone, fluticasone, fluticasone proprionate, fluticasone furoate, mometasone furoate, hydrocortisone, triamcinolone, nandrolone decanoate, neomycin sulphate, rimexolone, methylprednisolone and prednisolone;

2) antibiotic and antibacterial agents such as, for example, metronidazole, sulphadiazine, triclosan, neomycin, amoxicillin, amphotericin, clindamycin, aclarubicin, dactinomycin, nystatin, mupirocin and chlorhexidine;

3) systemically active drugs such as, for example, isosorbide dinitrate, isosorbide mononitrate, apomorphine and nicotine;

4) antihistamines such as, for example, azelastine, chlorpheniramine, astemizole, cetitizine, cinnarizine, desloratadine, loratadine, hydroxyzine, diphenhydramine, fexofenadine, ketotifen, promethazine, trimeprazine and terfenadine;

5) anti-inflammatory agents such as, for example, piroxicam, benzydamine, diclofenac sodium, ketoprofen, ibuprofen, heparinoid, nedocromil, sodium cromoglycate, fasafungine and iodoxamide;

6) antimuscarinic/anticholinergic agents such as, for example, atropine, benzatropine, biperiden, cyclopentolate, oxybutinin, orphenadine hydrochloride, procyclidine, propantheline, propiverine, tiotropium, tropicamide, trospium, ipratropium bromide, GSK573719 and oxitroprium bromide;

7) anti-emetics such as, for example, bestahistine, dolasetron, nabilone, prochlorperazine, ondansetron, trifluoperazine, tropisetron, domperidone, hyoscine, cinnarizine, metoclopramide, cyclizine, dimenhydrinate and promethazine;

8) hormonal drugs such as, for example, protirelin, thyroxine, salcotonin, somatropin, tetracosactide, vasopressin or desmopressin;

9) bronchodilators, such as salbutamol, fenoterol, formoterol, indacaterol, vilanterol and salmeterol;

10) sympathomimetic drugs, such as adrenaline, noradrenaline, dexamfetamine, dipirefin, dobutamine, dopexamine, phenylephrine, isoprenaline, dopamine, pseudoephedrine, tramazoline and xylometazoline;

11) anti-fungal drugs such as, for example, amphotericin, caspofungin, clotrimazole, econazole nitrate, fluconazole, ketoconazole, nystatin, itraconazole, terbinafine, voriconazole and miconazole;

12) local anaesthetics such as, for example, amethocaine, bupivacaine, hydrocortisone, methylprednisolone, prilocaine, proxymetacaine, ropivacaine, tyrothricin, benzocaine and lignocaine;

13) opiates, such as for pain management, such as, for example, buprenorphine, dextromoramide, diamorphine, codeine phosphate, dextropropoxyphene, dihydrocodeine, papaveretum, pholcodeine, loperamide, fentanyl, methadone, morphine, oxycodone, phenazocine, pethidine and combinations thereof with an anti-emetic;

14) analgesics and drugs for treating migraine such as clonidine, codine, coproxamol, dextropropoxypene, ergotamine, sumatriptan, tramadol and non-steroidal anti-inflammatory drugs;

15) narcotic agonists and opiate antidotes such as naloxone, and pentazocine;

16) phosphodiesterase type 5 inhibitors, such as sildenafil; and/or 17) pharmaceutically acceptable salts of any of the foregoing.

In one embodiment, the additional active agents are pharmaceutically active agents which are known to be useful in the treatment of respiratory disorders, such as β2-agonists, steroids, antimuscarinics/anticholinergics, phosphodiesterase 4 inhibitors, and the like.

In one embodiment, the pharmaceutical composition according to the subject invention comprises one or more inhibitors of a lncRNA and a pharmaceutically acceptable carrier, the inhibitor comprising 1) one or more antisense oligonucleotides that target the lncRNA; and/or 2) one or more nucleic acid sequences that are complementary to at least 10 contiguous nucleotides of the nucleotide sequence of the lncRNA. The lncRNA is selected from, for example, lncRNA AL357060.1, AC011511.2 and AC007389.1.

In one embodiment, the composition is formulated in accordance with routine procedures as a pharmaceutical composition adapted for local administration to human beings. Typically, compositions for local administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile water for injection or saline can be provided so that the ingredients may be mixed prior to administration.

The therapeutic or pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The present invention also provides for the modification of the compound such that it is more stable once administered to a subject, i.e., once administered it has a longer time period of effectiveness as compared to the unmodified compound. Such modifications are well known to those of skill in the art, e.g., microencapsulation, etc. The amount of the therapeutic or pharmaceutical composition of the invention which is effective in the treatment of a particular disease, condition or disorder will depend on the nature of the disease, condition or disorder and can be determined by standard clinical techniques. In general, the dosage ranges from about 0.001 mg/kg to about 500 mg/kg.

In addition, in vitro assays may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems. For example, in order to obtain an effective mg/kg dose for humans based on data generated from rat studies, the effective mg/kg dosage in rats is divided by six.

For instance, suitable unit dosages may be between about 0.01 to about 500 mg, about 0.01 to about 300 mg, about 0.01 to about 200 mg, about 0.01 to about 100 mg, about 0.01 to about 50 mg, about 0.01 to about 30 mg, about 0.01 to about 20 mg, about 0.01 to about 10 mg, about 0.01 to about 5 mg, about 0.01 to about 3 mg, about, 0.01 to about 1 mg, or about 0.01 to about 0.5 mg. Such a unit dose may be administered more than once a day, e.g. two or three times a day, for a period of time, e.g., one week, ten days, two weeks, one month, two months, three months, six months, one year or longer.

The compositions of the present invention can be administered to the subject being treated by standard routes, including the oral, ophthalmic, nasal, topical, transdermal, intra-articular, parenteral (e.g., intravenous, intraperitoneal, intradermal, subcutaneous or intramuscular), intracranial, intracerebral, intraspinal, intravaginal, intrauterine, or rectal route. Depending on the condition being treated, one route may be preferred over others, which can be determined by those skilled in the art. For instance, the compositions of the present invention can be nasally administered to the subject for treatment of conditions associated with airway inflammation.

Administration by inhalation is preferably as aerosol, dry powder or solution, preferably using a spacer, metered dose inhaler (MDI) or nebulizer. In one embodiment, the inhibitor(s) or pharmaceutical composition(s) is (are) administered to a subject in need thereof in combination with a second pulmonary therapy. Said second therapy preferably selected from a therapy or treatment with bronchodilators, such as short and long-acting b2-agonists, anticholinergic agents, inhaled corticosteroids (ICS), or inhaled mucolytics, such as DNAse, hypertonic saline.

In one embodiment, the composition of the present invention and any second anti-inflammatory agent are administered sequentially to the patient, with the anti-inflammatory agent being administered before, after, or both before and after treatment with the peptides of the present invention. Sequential administration involves treatment with the anti-inflammatory agent at least on the same day (within 24 hours) of treatment with peptides of the present invention and may involve continued treatment with the anti-inflammatory agent on days that the composition of the present invention is not administered.

The invention also provides a pharmaceutical pack or kit comprising one or more containers filled with one or more of the ingredients, e.g., inhibitor, carrier, of the pharmaceutical compositions of the invention. The kit may also comprise an inhaler.

Method of Use

The present invention provides novel and advantageous therapeutic methods for treating inflammation, in particular, airway inflammation, comprising administering to a subject in need of such treatment at least one inhibitor of a lncRNA or a pharmaceutical composition comprising at least one inhibitor of a lncRNA.

In one embodiment, the present invention provides a method for the prevention and/or treatment of a chronic pulmonary disease, comprising administering to a subject at least one inhibitor of a lncRNA or a pharmaceutical composition comprising at least one inhibitor of a lncRNA.

In one embodiment, the subject invention provides methods for treating pulmonary airway inflammation in a subject, the method comprising administering to the subject in need of such treatment a pharmaceutically effective amount of an antisense oligonucleotide that targets a lncRNA; a nucleic acid sequence that is complementary to at least 10 contiguous nucleotides of the nucleotide sequence of said lncRNAs; or a combination thereof.

In one embodiment, the subject invention provides a method of identifying a chronic pulmonary disease in a subject, the method comprising:

(a) determining the level of at least one lncRNA in:
i) a test sample obtained from the subject, and
ii) optionally, a control sample;
(b) optionally, obtaining at least one reference value corresponding to the level of at least one lncRNA; and
(c) identifying the chronic pulmonary disease in a subject based on the levels of at least one lncRNAs in the test sample and optionally, administering a therapy to the subject to treat and/or manage the chronic pulmonary disease, or
(d) identifying an absence of the chronic pulmonary disease in the subject based on the level of at least one lncRNA in the test sample and withholding the therapy to the subject to treat and/or manage the chronic pulmonary disease.

In one embodiment, the subject invention provides a method of identifying a pulmonary airway inflammation in a subject, the method comprising:

(a) determining the level of at least one lncRNA in:
 i) a test sample obtained from the subject, and
 ii) optionally, a control sample;
(b) optionally, obtaining at least one reference value corresponding to the level of at least one lncRNA; and
(c) identifying the pulmonary airway inflammation in a subject based on the levels of at least one lncRNAs in the test sample and optionally, administering a therapy to the subject to treat and/or manage the pulmonary airway inflammation, or
(d) identifying an absence of the pulmonary airway inflammation in the subject based on the level of at least one lncRNA in the test sample and withholding the therapy to the subject to treat and/or manage the pulmonary airway inflammation.

The term "sample" as used herein refers to any physical sample that includes a cell or a cell extract from a cell, a tissue, a biofluid or an organ including a biopsy sample. The sample can be from a biological source such as a subject, or a portion thereof, or can be from a cell culture. Samples from a biological source can be from a normal or an abnormal organism, such as an organism known to be suffering from a condition or a disease state, or any portion thereof. Samples can also be from any fluid, tissue or organ including normal and abnormal (diseased) fluid, tissue or organ. Samples from a subject can be used, processed or cultured such that cells from the sample can be sustained in vitro as a primary or continuous cell culture or cell line.

In certain embodiments, the chronic pulmonary diseases can be asthma or chronic obstructive lung diseases including cystic fibrosis (CF), chronic lung disease (CLD) of prematurity (also known as bronchopulmonary dysplasia; BPD), chronic bronchitis (CB), emphysema, and chronic obstructive pulmonary disease (COPD). Cigarette Smoke induced COPD with chronic bronchitis and/or emphysema has evolved as the fourth leading cause of death worldwide. All chronic obstructive lung diseases are accompanied by various degrees of airway mucus obstruction, goblet cell metaplasia and chronic inflammation of the respiratory tract and the formation of emphysema, e.g., disturbance in the development and/or destruction of alveoli, ultimately resulting in respiratory insufficiency.

In one embodiment, the subject in need of treatment is diagnosed with an inflammatory disease or immune disorder that can be treated in accordance with the present invention. In one embodiment, the present invention comprises: diagnosing whether the subject has an inflammatory disease or immune disorder that can be treated in accordance with the present invention.

In one embodiment, the subject is suffering from a respiratory condition, such as a condition selected from: chronic obstructive pulmonary disease (COPD), asthma, cystic fibrosis (CF) and related airway diseases. In specific embodiments, the subject is suffering from overproduction of mucus. The subject may also include patients that are unable to produce mucus or mount appropriate inflammatory response.

In a further embodiment, the subject is suffering from COPD. In specific embodiments, the subject is suffering from COPD having a severity of global initiative for COPD (GOLD) stage 0, 1, 2, 3, or 4. The GOLD system categorizes COPD into stages based on airflow limitations, for example, post-bronchodilator FEV1 (Table 1). Subject having a GOLD stage 0 is a subject at risk of developing COPD.

TABLE 1 classification in COPD

| GOLD stage | COPD severity | FEV1/FVC ratio | FEV1 range |
| --- | --- | --- | --- |
| 1 | mild | <0.70 | ≥80% of normal |
| 2 | moderate | <0.70 | 50%-79% of normal |
| 3 | severe | <0.70 | 30%-49% of normal |
| 4 | Very servere | <0.70 | <30% of normal |

The term "subject" or "patient," as used herein, describes an organism, including mammals such as primates, to which diagnosis, prognosis, prevention and/or treatment with the compositions according to the present invention can be provided. Mammalian species that can benefit from the disclosed methods of treatment include, but are not limited to, apes, chimpanzees, orangutans, humans, monkeys; domesticated animals such as dogs, cats; live stocks such as horses, cattle, pigs, sheep, goats, chickens; and other animals such as mice, rats, guinea pigs, and hamsters.

In one embodiment, the terms "inflammation" and "inflammatory response" include immune-related responses and/or allergic reactions to a physical, chemical, or biological stimulus. For example, inflammation for which the primary activating inflammation is antigen-derived can be due to, for example, bacterial lipopolysaccharide. The terms "inflammation" and "inflammatory response" also include inflammation associated with chronic pulmonary diseases In one embodiment, the method according to the subject invention comprises determining lncRNAs expression levels in a sample, e.g., patient specimen. The patient specimen comprises preferably sputum, bronchoalveolar lavage fluid, blood, urine, airway and/or lung tissue. In a preferred embodiment, the patient specimen comprises AECs. An upregulation of lncRNAs expression compared to a normal or control sample is indicative of a chronic pulmonary disease or airway inflammation.

In one embodiment, the present invention provides a method for identifying a modulator of a lncRNA, comprising: contacting a cell with a candidate compound; assessing the lncRNA activity or expression; and comparing the activity or expression with the activity or expression in the absence of the candidate compound, wherein a difference between the measured activities or expression indicates that the candidate compound is a modulator of the lncRNA. Preferably, the modulator of lncRNAs is an inhibitor of lncRNAs.

In one embodiment, the present invention provides a method for treating inflammatory diseases and immune disorders, wherein the method comprises administering, to a subject in need of such treatment, an effective amount of a modulator/inhibitor of a lncRNA selected from lncRNA AL357060.1, AC011511.2 and AC007389.1.

In one embodiment, the prevention and/or treatment of the chronic pulmonary disease comprises inhibiting lncRNAs expression and/or activity and/or function. LncRNAs activity and/or expression and/or function can be inhibited in different ways, such as by using antisense oligonucleotides or oligonucleotides that are complementary to the nucleotide sequence of the target lncRNA as inhibitors, which are preferably chemically modified. DNA vector systems or viral vector systems can be used that express the antisense or complementary oligonucleotides; liposomes delivering the antisense or complementary oligonucleotides can be utilized.

Preventive treatment is performed by initiating therapy prior to the onset of chronic and irreversible lung changes such as bronchiectasis, airway remodelling and emphysema. This is facilitated by early diagnosis using the new specific diagnostic marker according to the invention. Treatment preferably means initiation of therapy after the diagnosis has been established, which in general also implicates the development of chronic lung lesions including e.g. bronchiectasis, airway remodelling and emphysema. For both, treatment is preferably performed by inhalation therapy (aerosol, dry powder, solution) with an appropriate device.

In one embodiment, the subject invention provides a method for treating pulmonary airway inflammation in a subject, the method comprising:
 (a) determining the level of at least one lncRNA in:
  i) a test sample obtained from the subject, and
  ii) optionally, a control sample;
 (b) optionally, obtaining at least one reference value corresponding to the level of at least one lncRNA;
 (c) identifying the pulmonary airway inflammation in the subject based on the levels of at least one lncRNAs in the test sample; and
 (d) administering a therapy to the subject to treat and/or manage the pulmonary airway inflammation.

In one embodiment, the therapy to the subject to treat the pulmonary airway inflammation comprising administering to the subject a pharmaceutically effective amount of 1) one or more antisense oligonucleotides that target one or more lncRNAs that are upregulated in the pulmonary airway inflammation; or 2) a nucleic acid sequence that is complementary to at least 10 contiguous nucleotides of the nucleotide sequence of the one or more lncRNA. Preferably, one or more lncRNAs are selected from AL357060.1, AC011511.2 and AC007389.1.

In one embodiment, the control sample is obtained from: i) an individual belonging to the same species as the subject and not having pulmonary airway inflammation, or ii) the subject at a prior time known to be free from pulmonary airway inflammation.

The present invention provides novel and advantageous therapeutic methods for treating inflammation, in particular, airway inflammation, comprising administering to a subject in need of such treatment a pharmaceutically effective amount of 1) one or more antisense oligonucleotides that target one or more lncRNAs that are upregulated in inflammation, in particular, airway inflammation, 2) a nucleic acid sequence that is complementary to at least 10 contiguous nucleotides of the nucleotide sequence of lncRNA, lncRNA being selected from AL357060.1, AC011511.2 and AC007389.1, or 3) a combination thereof.

In one embodiment, the present invention provides a method for the prevention and/or treatment of a chronic pulmonary disease, comprising administering to a subject in need of such prevention and/or treatment a pharmaceutically effective amount of 1) one or more antisense oligonucleotides that target one or more lncRNAs that are upregulated in chronic pulmonary disease, in particular COPD, 2) a nucleic acid sequence that is complementary to at least 10 contiguous nucleotides of the nucleotide sequence of lncRNA, lncRNA being selected from AL357060.1, AC011511.2 and AC007389.1, or 3) a combination thereof.

In one embodiment, the present invention provides a method for treating COPD, comprising administering to a subject having been diagnosed with COPD a pharmaceutically effective amount of 1) one or more antisense oligonucleotides that target one or more lncRNAs that are upregulated in COPD, 2) a nucleic acid sequence that is complementary to at least 10 contiguous nucleotides of the nucleotide sequence of the lncRNA, or 3) a combination thereof. The lncRNA is selected from AL357060.1, AC011511.2 and AC007389.1. In a further embodiment, the COPD is triggered by smoking.

In one embodiment, the method may comprise a step of determining the levels of lncRNA in a sample of the subject prior to the administration and/or after the administration of the inhibitor.

In one embodiment, the present invention provides a method for treating a subject having a risk of developing COPD, the method comprising administering to the subject a pharmaceutically effective amount of 1) one or more antisense oligonucleotides that target one or more lncRNAs, 2) a nucleic acid sequence that is complementary to at least 10 contiguous nucleotides of the nucleotide sequence of the lncRNA, or 3) a combination thereof. The lncRNA is selected from, for example, AL357060.1, AC011511.2 and AC007389.1. In a further embodiment, the subject is a smoker.

A further embodiment of the invention provides a method for monitoring the effect of a treatment for a chronic pulmonary disease in a subject. A method for monitoring the effect of a treatment for a chronic pulmonary disease in a subject can comprise:
 (a) determining the level of at least one lncRNAs in:
  i) a pre-treatment test sample obtained from the subject before the treatment,
  ii) a post-treatment test sample obtained from the subject after the treatment, and
  ii) optionally, a control sample;
 (b) optionally obtaining at least one reference values corresponding to levels of at least one lncRNAs; and
 (c) identifying the treatment for a chronic pulmonary disease in the subject as effective based on the levels of at least one lncRNAs in the post-treatment test sample compared to the levels of at least one lncRNAs in the pre-treatment test sample and optionally, continuing the treatment for the chronic pulmonary disease in the subject, or
 (d) identifying the treatment for the chronic pulmonary disease in the subject as ineffective based on the levels of at least one lncRNAs in the post-treatment test sample compared to the levels of at least one lncRNAs in the pre-treatment test sample and optionally, modifying the treatment in the subject.

In one embodiment, the present invention provides a method for accessing the progression of an airway inflammation in a subject who is undergoing treatment for the airway inflammation, the method comprises:
 (i) assessing the expression level of at least one lncRNA in a sample obtained from the subject;
 (ii) comparing the expression level of at least one lncRNA in the sample to a reference derived from the expression level of at least one lncRNA in samples obtained from healthy subjects and determining the current condition of the subject; and
 (iii) for the subject determined to suffer from the airway inflammation periodically repeating steps (i) and (ii) during treatment as a basis to determine the efficacy of said treatment by assessing whether the expression level of at least one lncRNA in the subject is up-regulated or down-regulated, wherein a down-regulation in the expression level of at least one lncRNA correlates to an improvement in the subject's condition.

In one embodiment, the subject invention provides methods for reducing, blocking and/or inhibiting the expression and/or activities of lncRNAs in a subject in need of such inhibition. The method comprises administering to the subject a pharmaceutical composition according to the subject invention. In a further embodiment, the pharmaceutical composition comprises, or consists of, a pharmaceutically effective amount of one or more inhibitors of one or more lncRNAs. Preferably, the inhibitor of lncRNAs comprises, or consists of, 1) one or more antisense oligonucleotides that target one or more lncRNAs, 2) a nucleic acid sequence that is complementary to at least 10 contiguous nucleotides of the nucleotide sequence of the lncRNA, and/or 3) a combination thereof. The lncRNA is selected from, for example, AL357060.1, AC011511.2 and AC007389.1.

In specific embodiments, the subject may be diagnosed with pulmonary airway inflammation, asthma, cystic fibrosis (CF), bronchopulmonary dysplasia (BPD), chronic bronchitis (CB), emphysema, or chronic obstructive pulmonary diseases (COPD).

In one embodiment, the subject invention also provides methods for reducing the overproduction of mucus in the lungs and/or airways of a subject. The method comprises administering to the subject a pharmaceutical composition according to the subject invention.

In one embodiment, the subject invention further provides strategies and methods for preventing and/or treating a subject having pulmonary diseases with impaired mucus production or inflammatory response. The subject may not be able to produce mucus or mount appropriate inflammatory response. The methods utilize the ectopic overexpression of the lncRNAs or mimics to improve the health or condition of the patient.

In a further embodiment, the method for improving mucus production in a subject comprises administering to a subject in need of such improvement a pharmaceutically effective amount of 1) a nucleic acid sequence comprising one or more lncRNAs of the subject invention or fragments thereof, 2) a vector comprising a nucleic acid sequence of one or more lncRNAs of the subject invention or fragments thereof, and/or 3) a cell that overexpresses a nucleic acid sequence of one or more lncRNAs of the subject invention or fragments thereof. In a specific embodiment, the cell is AEC.

The tennis "treatment" or any grammatical variation thereof (e.g., treat, treating, etc.), as used herein, includes but is not limited to, the application or administration to a subject (or application or administration to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of a pathology or condition, including any objective or subjective parameter such as abatement; remission; lessening of the rate of worsening; lessening severity of the disease; stabilization, diminishing of symptoms or making the pathology or condition more tolerable to the subject; or improving a subject's physical or mental well-being. Treating can also include preventing a condition or disorder, which, as used herein, means delaying the onset of or progression of a particular sign or symptom of the condition or disorder.

The term "prevention" or any grammatical variation thereof (e.g., prevent, preventing, etc.), as used herein, includes but is not limited to, at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). The term "prevention" may refer to avoiding, delaying, forestalling, or minimizing one or more unwanted features associated with a disease or disorder, and/or completely or almost completely preventing the development of a disease or disorder and its symptoms altogether. Prevention can further include, but does not require, absolute or complete prevention, meaning the disease or disorder may still develop at a later time and/or with a lesser severity than it would without preventative measures. Prevention can include reducing the severity of the onset of a disease or disorder, and/or inhibiting the progression thereof.

Various techniques are well known to a person of ordinary skill in the art to determine the level of lncRNAs in a sample. Non-limiting examples of such techniques include microarray analysis, real-time polymerase chain reaction (PCR), Northern blot, in situ hybridization, solution hybridization, and quantitative reverse transcription PCR (qRT-PCR). Methods for carrying out these techniques are routine in the art. Additional methods of determining the level of lncRNA in a sample are also well known to a person of ordinary skill in the art and such embodiments are within the purview of the invention.

In molecular hybridization, a labeled DNA or RNA sequence is used as a probe to identify or quantify the counterpart of the sequence in a biological sample. Molecular hybridization could be used to identify the position of DNA or RNA sequences in situ (i.e., in their natural positions within a chromosome). In one embodiment, the label can be a radioactive agent. The radioactive copies of a DNA or RNA sequence could be used to detect complementary DNA or RNA sequences. In certain embodiments, fluorescent labels can be used in hybridization probes. The fluorescent labels provide advantageous properties because of their greater safety, stability, and ease of detection.

In general, the first step in the in-situ hybridization is to identify a probe sequence that can hybridize with the target sequence. Then, the probe sequence may be labeled with a fluorescent agent to make a fluorescent copy of the probe sequence. The probe sequence may also be modified with a labeled that can bind to a secondary fluorescent label. Next, before any hybridization can occur, both the target and the probe sequences must be denatured with, for example, heat or chemicals. This denaturation step is necessary in order for new hydrogen bonds to form between the target and the probe sequences during the subsequent hybridization step. The probe and target sequences are then mixed together, and the probe specifically hybridizes to its complementary sequence on target sequence.

When the probe sequence is directly labeled with the fluorescent agent, the target sequence can be detected directly. On the other hand, when the probe sequence is indirectly labeled, an additional step may be needed to visualize the hybridized probe, for example, by a secondary fluorescent agent that recognizes the first label on the probe sequence.

In certain embodiments, the control sample and the test sample are obtained from the same type of a body fluid. Non-limiting examples of the body fluids that can be used as samples include, urine, aqueous humor, vitreous humor, bile, blood, cerebrospinal fluid, chyle, endolymph, perilymph, lymph, mucus (including nasal drainage and phlegm), pericardial fluid, peritoneal fluid, pleural fluid, pus, rheum, saliva, sputum, synovial fluid, vaginal secretion, blood, serum or plasma. Additional examples of body fluids are well known to a person of ordinary skill in the art and such embodiments are within the purview of the invention.

Once improvement of the patient's condition has occurred, a maintenance dose is administered if necessary. Subsequently, the dosage or the frequency of administration, or both, may be reduced as a function of the symptoms to a level at which the improved condition is retained. When the symptoms have been alleviated to the desired level, treatment should cease. Patients may however require intermittent treatment on a long-term basis upon any recurrence of disease symptoms.

The subject invention encompasses the use of sequences having a degree of sequence identity with the nucleic acid sequence(s) of the present invention. A similar sequence is taken to include a nucleotide sequence which may be, at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the subject sequence. Typically, the similar sequences will comprise the same or similar secondary structure as the subject nucleic acid aptamer. In one embodiment, a similar sequence is taken to include a nucleotide sequence which has one or several additions, deletions and/or substitutions compared with the subject sequence.

As used herein, the singular forms "a," "an" and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise," can be used interchangeably.

The phrases "consisting essentially of" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

The term "effective amount," as used herein, refers to an amount that is capable of treating or ameliorating a disease or condition or otherwise capable of producing an intended therapeutic effect.

The term "about" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients where the term "about" is used, these compositions contain the stated amount of the ingredient with a variation (error range) of 0-10% around the value (X±10%).

EXAMPLES

Experimental Section

Materials

Sequence of Exon 1, 2 and 3 of lncRNA AC011511.2, the sequences targeted by the siRNAs designed for the respective exons, and PCR primers for lncRNAs are listed below:

Exon 1:
(SEQ ID NO: 1)
5'-ggaggataca acaggcggtg aggattgcat taggtccatg gccctgccc ccacccagct ctgcccgccg gctcactcac agagcacatt cacggtcacc ttgcgggtga cctccccttg agtgctcctg gcccgacaga g-3'

Exon 2:
(SEQ ID NO: 2)
5'-gaagtcactc tgaaaactca ggtttacaca acatctactt gtacaatcaa gcacacactc tcaggctgca tgaagtactg tcgcagacag gactgcaaac cctctcaggg gtgagaatgg ctggcagcag tgctcaggag agggatgtgg caggagtcag ctcctaggaa gtgccagcgc ccacgcacct gtgagctcct ggagtctgac tcaccgg-3'

Exon 3:
(SEQ ID NO: 3)
5'-gtggagaaac ggaggctgta gaaatacagc actttcccaa gggtacaagc ccaaagtcat cgtgactcct gaaatcccgc tcttcatccc tctgccactc agttcaccat tacagccctc gctcacctgg gcgcggtggc gaaaacatcg gggtgcaggt cggccaggcc cacgcgctcc tgctcgaagc cccgcaagga ctcgacccag gcctgcactg ggcgtcgatg agtgggtacc gggagctcga ctttgcgcag cacgggctcc gggagacctg gagcgattgc gggggtcaga ggttagggtc aagggtcaga cctctctgtc gccgccctc ctggagccac cccggttgcc ttaccctcgc tcgccacctg ctccgggttc tcggtcgcac gcgctgcctc ttccgccagg gaactcaggc cctgcaaggg ttgggcgaaa gtgagagacg acccctggac acccccaaat ttcatccttc gaccacgcct ccagcccctg gcctcacctg gctgccggta ggccgaagcc aggcccgcgc cccggcccgg-3'

X1 siRNA (6-30):
(SEQ ID NO: 4)
5'-rArUrArCrArArCrArGrGrCrGrGrUrGrArGrGrArUrUrGrC

AT-3'
(sense strand)

-continued (SEQ ID NO: 5)
5'-ArUrGrCrArArUrCrCrUrCrArCrCrGrCrCrUrGrUrUrGrUr

ArUrCrC-3'
(antisense strand)

X2-A siRNA (26-50):
(SEQ ID NO: 6)
5'-rArCrArCrArArCrArUrCrUrArCrUrUrGrUrArCrArArUrC

AA-3'
(sense strand)

(SEQ ID NO: 7)
5'-rUrUrGrArUrUrGrUrArCrArArGrUrArGrArUrGrUrUrGrU rGrUrArA-3'
(antisense strand)

X2-B siRNA (35-59):
(SEQ ID NO: 8)
5'-rCrUrArCrUrUrGrUrArCrArArUrCrArArGrCrArCrArCrA

CT-3'
(sense strand)

(SEQ ID NO: 9)
5'-rArGrUrGrUrGrUrGrCrUrUrGrArUrUrGrUrArCrArArGrU rArGrArU-3'
(antisense strand)

X3 siRNA (37-61):
(SEQ ID NO: 10)
5'-rCrCrArArGrGrGrUrArCrArArGrCrCrCrArArArGrUrCrA

TC-3'
(sense strand)

(SEQ ID NO: 11)
5'-rGrArUrGrArCrUrUrUrGrGrGrCrUrUrGrUrArCrCrCrUrU rGrGrGrA-3'
(antisense strand)

X1 lncRNA-A (16-95; 79 bp amplicon, Tm-62o C., GC
content - 50%)
(SEQ ID NO: 12)
Forward 5' CGGTGAGGATTGCATTAGGT 3'
(Sense)

(SEQ ID NO: 13)
Reverse 5' CGTGAATGTGCTCTGTGAGT 3'
(AntiSense)

X1 lncRNA-B (9-105; 109 bp amplicon, Tm-63o C., GC
content - 57.9% fwd and 52.6 rev)
(SEQ ID NO: 14)
Forward 5' CAACAGGCGGTGAGGATTG 3'
(Sense)

(SEQ ID NO: 15)
Reverse 5' GCAAGGTGACCGTGAATGT 3'
(AntiSense)

Target sequence of X1 siRNA (6-30):
(SEQ ID NO: 16)
5'-atacaacaggcggtgaggattgcat-3'

Target sequence of X2-A siRNA (26-50):
(SEQ ID NO: 17)
5'-acacaacatctacttgtacaatcaa-3'

Target sequence of X2-B siRNA (35-59):
(SEQ ID NO: 18)
5'-ctacttgtacaatcaagcacacact-3'

Target sequence of X3 siRNA (37-61):
(SEQ ID NO: 19)
5'-ccaagggtacaagcccaaagtcatc-3'

TABLE 2

Quantitative PCR primers custom made from Applied Biosystems (Thermo-Fisher Inc.)

| Probe | Target Sequence | Location on NCBI Assembly (Chromosome 19) | Reporter Dye | Reporter Quencher |
|---|---|---|---|---|
| lncRNA-X1 | CTCTGCCCGCCGGCTCACTCACAGA (SEQ ID NO: 20) | 10285108 | FAM | NFQ |
| lncRNA-X2 | CTCTCAGGGGTGAGAATGGCTGGCA (SEQ ID NO: 21) | 10260428 | FAM | NFQ |
| lncRNA-X3 | GCTCCGGGAGACCTGGAGCGATTGC (SEQ ID NO: 22) | 10252827 | FAM | NFQ |

Sequence of lncRNA AL357060.1 (AL35, ENST00000606998.1), sequences of Exon 1, 2, 3 and 4 of lncRNA AL357060.1, the sequences targeted by the siRNAs designed for the respective exons, and PCR primers for lncRNAs are listed below:

```
SEQ ID NO: 23 (ENST00000606998.1 AL357060.1-202
cDNA):
ACTGCTTTTCTGAGAGGCCAGGTGGCAGGATGTGGGACGACTCCAGCTGA

CAAAGACAGTCTAACCGTGGGGTAGGGGCTGGAGCAGGGGCCAGCGACCC

ACGTCTACATGCATACTTCTCTTACACTGCTGCTACTGGAAAAGCTGAAC

CCCGCGCCAGGACCCCAGCCCCCTGCAAGGACCCGTGAGCGTCTGGGAAG

CTGTCTCTGGGACTGAAGCCCCCCACCTCCGCCGGGCTGGCGGCCACTGC

GGTACCCTACGCCCCGTCGGGCTGGTCCTGCACAATTTGGGAAAAAGCCG

CAGCGCTTCTGCAAGGTCTACGTGGCCATGAGCATGCAACGCTTGGCTCC

AAAAAAGACACGAAAGGAGCAAAGCGCCAACGACCACCCGATCGGAGGGC

CCGAGGGGCGCCTCTTCACCAGTCAGCTGCAGCTTAAGTTCCGTGCATTA

TCTGAAAGGAACAGCTGGCTGGAGGTATCCAGGGCTGTCACTCCAACCTC

TGCAGCAGTGACCTCAACTCCCAGCACTTCAAAACCCAGACAGAAACGTC

CAACAAACTCCCAGTCCAGGAGCGCTGCAAAACCAACGCCAGTTGTTTTT

CTGCAGAAAATCATCAACTGTGGAGAAGAAGAAGGGAAATAAGAAAGAAA

GAAAACCCTAAAAACCACCCTGGCGCCCGGGCCCGCAGGCCTCGGGCCGG

CTCTGAAAAGTTTGGGCTGTGCACGTGATGAGCGCGTAGGCGGGAGCCCC

AGACAGGACCCGGGCGGGCATTTCGAGAAAAAGCAGCGGTGACAGCCTTT

GGTCCCCATCTCCATTGTTCCTGCCAGCTCTGGACCCCAGGCTGCATGAG

ACGTAGGTCCCAGGGGACACCCGACCCCGTGGCCCCAGTCTTAGCTTCCA

CTGCCCCTATCTGGCTCATGTCTTGCTGTCTGGTGTCATGAACTGGGAGT

GCAGTAAAGAGGAGTGACAAGCCTGAGGGGCCACGTTCATACCTGCCACT

GCCAACTGTCCTGATGTAACTGCTTTGTCATCTTGCCTGCCAGGATTTGT

GACAAGGGCAAGAATCTTCTGTTCCATATGCAACATCTTCTGGCAGCCTT

GTCCTTTTTCTGTCCTTGACGACTACAATAACAAACAGCTGTTGCCGAGG

CATTGCTGTTGACGTGTTACCTTTGAAACCTCCCTCCTGTTATGGAATAA

GCCTCTTCCAGATCATGGCTCATTATCATCTAGTCTGACAAGCAGCCTTG

TTGCCACGGAGACCCAAAGGGATCAGGCGTGGCATTTGCCTGCATCATCA

CCCCCTCCAGGGGAACTATAAGGACTCTTCTGTGCGTCATGCGTGGCTGT

CCTGGGACTGGCTGCCACCAGACTTTTCCTGCGGGTAAAACCTAAACAAA

TGATCAGCTGCAGATAATATCAAGACCTCTGTTTGATATGTTAATAGTGA

CAGCCAGATTTCCACAATTAACAACGAGGTGGGAAGAAAACACTGTAGTC

ACCAGACTTGGGAGGAGAGGGTTTGTATTCACATAAACACAACCTCACGT

CACTGCTTGCCACCACAAAGGGCTCTGTTCACTGTTTTGTTCTCAAAGAT

CATCCTTGCGCTCATCCTCTGATCTTGAATTTCTACATAACTTTCTCAGT

TTATATGCCCTGTGGCAAGTGCAGCAAGCACTGTTTCCTGTTTCTAAACT

TGTAGAAAATCATCCATACATCTTACAGTTGTCAGTTTTAACCAGATAAC

AGTGGCACTTTGTTGCTGCTTTTTTATCTTTAGCTTAGGTTAACAGGACC

CTGGAAGTAAAGTTGTTGATTTATTCAATAGAGTATTCTCAATTAATTTG

GCTAGATTTCTACATGATTCAAAATCTAAAAAAGTAGAAATGCATGCTTA

CATGTCTAAGGCCTGAAAAATTGGTAGTGACATCCCAAAATAAATGAAGG

TTTTAAAAC

SEQ ID NO: 24 (AL357060.1-202, ENSE00003696000,
exon 1):
ACTGCTTTTCTGAGAGGCCAGGTGGCAGGATGTGGGACGACTCCAGCTGA

CAAAGACAGTCTAACCGTGGGGTAGGGGCTGGAGCAGGGGCCAGCGACCC

ACGTCTACATGCATACTTCTCTTACACTGCTGCTACTGGAAAAGCTGAAC

CCCGCGCCAGGACCCCAGCCCCCTGCAAGGACCCGTGAGCGTCTGGGAAG

CTGTCTCTGGGACTGAAGCCCCCCACCTCCGCCGGGCTGGCGGCCACTGC

GGTACCCTACGCCCCGTCGGGCTGGTCCTGCACAATTTGGGAAAAAGCCG

CAGCGCTTCTGCAAGGTCTACGTGGCCATGAGCATGCAACGCTTGGCTCC

AAAAAAGACACGAAAGGAGCAAAGCGCCAACGACCACCCGATCGGAGGGC

CCGAGGGGCGCCTCTTCACCAGTCAGCTGCAGCTTAAGTTCCGTGCATTA

TCTGAAAGGAACAGCTGGCTGGAGGTATCCAGGGCTGTCACTCCAACCTC

TGCAGCAGTGACCTCAACTCCCAGCACTTCAAAACCCAGACAGAAACGTC

CAACAAACTCCCAGTCCAGGAGCGCTGCAAAACCAACGCCAG

SEQ ID NO: 25 (AL357060.1-202, ENSE00003695293,
exon 2):
TTGTTTTTCTGCAGAAAATCATCAACTGTGGAGAAGAAGAAGGGAAATAA

GAAAGAAAGAAAACCCTAAAAACCACCCTGGCGCCCGGGCCCGCAGGCCT

CGGGCCGGCTCTGAAAAGTTTGGGCTGTGCACGTGATGAGCGCGTAGGCG

GGAGCCCCAGACAGGACCCGGGCGGGCATTTCGAGAAAAAGCAGCGGTGA

CAGCCTTTGGTCCCCATCTCCATTGTTCCTGCCAGCTCTGGACCCCAGGC

TGCATGAGACGTAGGTCCCAGGGGACACCCGACCCCGTGGCCCCAGTCTT

AG

SEQ ID NO: 26 (AL357060.1-202, ENSE00003701226,
exon 3):
CTTCCACTGCCCCTATCTGGCTCATGTCTTGCTGTCTGGTGTCATGAACT

GGGAGTGCAGTAAAGAGGAGTGACAAGCCTGAGGGGCCACGTTCATACCT

GCCACTGCCAACTGTCCTGATGTAACTGCTTTGTCATCTTGCCTGCCAGG

ATTTGTGACAAG

SEQ ID NO: 27 (AL357060.1-202, ENSE00003700849,
exon 4):
GGCAAGAATCTTCTGTTCCATATGCAACATCTTCTGGCAGCCTTGTCCTT

TTTCTGTCCTTGACGACTACAATAACAAACAGCTGTTGCCGAGGCATTGC

TGTTGACGTGTTACCTTTGAAACCTCCCTCCTGTTATGGAATAAGCCTCT

TCCAGATCATGGCTCATTATCATCTAGTCTGACAAGCAGCCTTGTTGCCA

CGGAGACCCAAAGGGATCAGGCGTGGCATTTGCCTGCATCATCACCCCCT

CCAGGGGAACTATAAGGACTCTTCTGTGCGTCATGCGTGGCTGTCCTGGG

ACTGGCTGCCACCAGACTTTTCCTGCGGGTAAAACCTAAACAAATGATCA

GCTGCAGATAATATCAAGACCTCTGTTTGATATGTTAATAGTGACAGCCA

GATTTCCACAATTAACAACGAGGTGGGAAGAAAACACTGTAGTCACCAGA

CTTGGGAGGAGAGGGTTTGTATTCACATAAACACAACCTCACGTCACTGC
```

-continued

TTGCCACCACAAAGGGCTCTGTTCACTGTTTTGTTCTCAAAGATCATCCT

TGCGCTCATCCTCTGATCTTGAATTTCTACATAACTTTCTCAGTTTATAT

GCCCTGTGGCAAGTGCAGCAAGCACTGTTTCCTGTTTCTAAACTTGTAGA

AAATCATCCATACATCTTACAGTTGTCAGTTTTAACCAGATAACAGTGGC

ACTTTGTTGCTGCTTTTTTATCTTTAGCTTAGGTTAACAGGACCCTGGAA

GTAAAGTTGTTGATTTATTCAATAGAGTATTCTCAATTAATTTGGCTAGA

TTTCTACATGATTCAAAATCTAAAAAAGTAGAAATGCATGCTTACATGTC

TAAGGCCTGAAAAATTGGTAGTGACATCCCAAAATAAATGAAGGTTTTAA

AAC

TABLE 3 primer-probe set 1 for exon 3 of lncRNA AL357060.1

| | Start | Stop | Length | Tm | GC % |
|---|---|---|---|---|---|
| Forward<br>TGAACTGGGAGTGCAGTAAAG<br>(SEQ ID NO: 28)<br>(Sense) | 45 | 66 | 21 | 62 | 47.6 |
| Probe<br>TTCATACCTGCCACTGCCAACTGT<br>(SEQ ID NO: 29)<br>(Sense) | 92 | 116 | 24 | 68 | 50 |
| Reverse<br>GGCAAGATGACAAAGCAGTTAC<br>(SEQ ID NO: 30)<br>(AntiSense) | 122 | 144 | 22 | 62 | 45.5 |

TABLE 4 primer-probe set 2 for exon 4 of lncRNA AL357060.1

| | Start | Stop | Length | Tm | GC % |
|---|---|---|---|---|---|
| Forward<br>CAATTAACAACGAGGTGGGAAG<br>(SEQ ID NO: 31)<br>(Sense) | 409 | 431 | 22 | 61 | 45.5 |
| Probe<br>ACCAGACTTGGGAGGAGAGGGTTT<br>(SEQ ID NO: 32)<br>(Sense) | 445 | 469 | 24 | 69 | 54 |
| Reverse<br>GTGACGTGAGGTTGTGTTTATG<br>(SEQ ID NO: 33)<br>(AntiSense) | 476 | 498 | 22 | 62 | 45.5 |

Example 1—Trained Mucous Response in In-Vitro Differentiated Human AECs

Figure 1B:
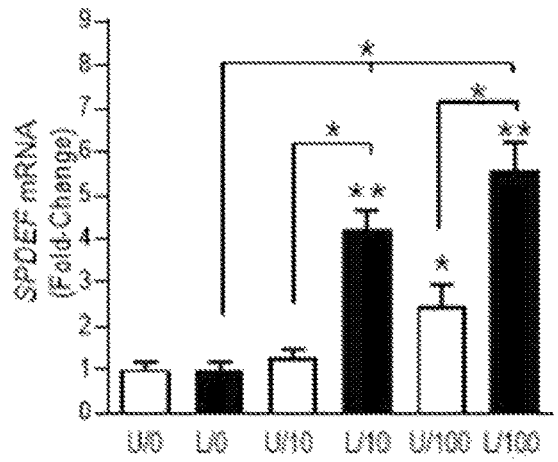

To determine the molecular pathways involved in the memory-based hyperreactive mucous response, primary human AECs were cultured and differentiated at the air-liquid interface (ALI). Differentiated human AECs were initially treated with 100 ng/ml LPS (L) or were left untreated (U), and then on day 10 were re-challenged with LPS at 0, 10 or 100 ng/ml. Groups were identified as U/0, U/10 and U/100 or L/0, L/10 and L/100, respectively. The LPS-pretreatment augmented the mucous phenotypalie as analyzed by MUC5AC (FIG. 1A) and SPDEF (FIG. 1B) mRNA levels compared to controls. The MUC5AC mRNA levels were induced >2-fold in L/0 AECs and were more than 10-fold induced by LPS challenge even with 10 ng/ml (L/1), a concentration that showed no effect on U/1 controls.

Figure 1C:
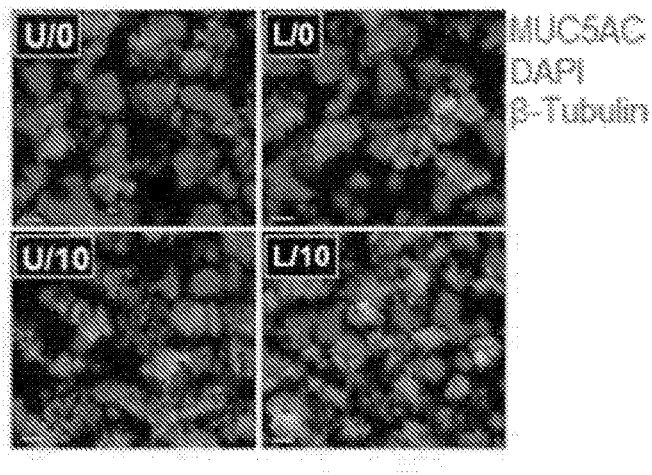
Figure 1D:
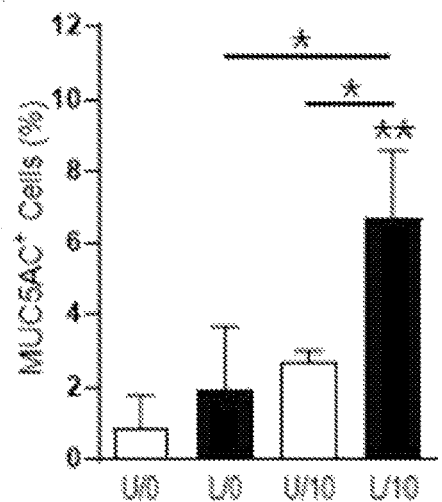

Similarly, SPDEF mRNA levels were more than 4-fold induced by LPS challenge in L/1 and L/10. The immunostaining for MUC5AC (FIG. 1C) showed a higher MUC5AC immunopositivity in L/10 compared to U/10 and other controls. Thus, the in-vitro differentiated human AECs could successfully model the LPS-induced mucous response.

Example 2—Transcriptomic Analysis of AECs

To help understand the genetic, the transcriptomic analyses of LPS-treated AECs were performed. Primary human AECs were differentiated at the ALI and were treated with LPS (100 ng/ml) for 2 h. Total RNA was isolated from cells and transcriptomic analysis was performed. Illumina TruSeq Stranded Total RNAseq libraries with ribosomal depletion were prepared per manufacturer's instructions. RNASeq data was aligned to the GRCh38 reference genome with Hisat2 and assembled into transcripts with Cufflinks2. DESeq2 was used to analyze the differential expression between treatments. Counts data from DESeq2 were normalized as read per million. Any gene that didn't have at least one read in 50% of the samples was removed from the analysis leaving a total of 15,148 genes that were relatively expressed (FIG. 2A). Expression analysis was performed with JMP Genomics 8. Counts were log 2(x+1) transformed and ANOVA with 5% FDR was performed. ToppFun was utilized for functional annotation pathway analysis that provided a molecular signature for LPS responsive transcripts (FIG. 2B).

Example 3—Identification of Novel Long Non-Coding RNAs in AECs

Eleven putative lncRNAs were identified. Their expression can be strongly induced. Five lncRNAs were down-regulated in differentiated human AECs following LPS treatment. Three lncRNAs: AL357060.1 (ENSG00000237499), AC011511.2 (ENSG00000266978) and AC007389.1 (ENSG00000204929) were selected for further analyses. The lncRNAs were selected based on the transcript that was among the top differentially expressed lncRNAs, by careful alignment and mapping for possible miRNA associations. The sequence information of exon 1, 2 and 3 of lncRNA AC011511.2 is shown in Table 5.

TABLE 5

Sequence information for Exon 1, 2 and 3 of lncRNA AC011511.2

| SEQ ID NO: | Exon No. | Exon/Intron | Start | End | Length (bp) | Sequence | Opposite strand |
|---|---|---|---|---|---|---|---|
| 1 | 1 | ENSE00002735766 | 10,285,108 | 10,284,968 | 141 | GGAGGATACAACAGGCGGTGAGGATTGCATT AGGTCCATGGCCCCTGCCCCCACCCAGCTCT GCCCGCCGGCTCACTCACAGAGCACATTCAC GGTCACCTTGCGGGTGACGCCCCTTGAGTGC TCCTGGCCCGACAGAG | ICAM-1 (Exon 4) |
| 2 | 2 | ENSE00002951147 | 10,260,428 | 10,260,212 | 217 | GAAGTCACTCTGAAAACTCAGGTTTACACAA CATCTACTTGTACAATCAAGCACACACTCTC AGGCTGCATGAAGTACTGTCGCAGACAGGAC TGCAAACCCTCTCAGGGGTGAGAATGGCTGG CAGCAGTGCTCAGGAGAGGGATGTGGCAGGA GTCAGCTCCTAGGAAGTGCCAGCGCCCACGC ACCTGTGAGCTCCTGGAGTCTGACTCACCGG | intergnic |
| 3 | 3 | ENSE00002791986 | 10,252,827 | 10,252,268 | 560 | GTGGAGAAACGGAGGCTGTAGAAATACAGCA CTTTCCCAAGGGTACAAGCCCAAAGTCATCG TGACTCCTGAAATCCCGCTCTTCATCCCTCT GCCACTCAGTTCACCATTACAGCCCTCGCTC ACCTGGGCGCGGTGGCGAAAACATCGGGGTG CAGGTCGGCCAGGCCCACGCGCTCCTGCTCG AAGCCCCGCAAGGACTCGACCCAGGCCTGCA CTGGGCGTCGATGAGTGGGTACCGGGAGCTC GACTTTGCGCAGCACGGGCTCCGGGAGACCT GGAGCGATTGCGGGGGTCAGAGGTTAGGGTC AAGGGTCAGACCTCTCTGTCGCCGCCCCTCC TGGAGCCACCCCGGTTGCCTTACCCTCGCTC GCCACCTGCTCCGGGTTCTGGTCGCACGCGC TGCCTCTTCCGCCAGGGAACTCAGGCCCTGC AAGGGTTGGGCGAAAGTGAGAGACGACCCCT GGACACCCCAAATTTCATCCTTCGACCACGC CTCCAGCCCTGGCCTCACCTGGCTGCCGGT AGGCCGAAGCCAGGCCCGCGCCCCGGCCCGG | MRPL4 (Ex 1-3) |

AL357060.1 lncRNA comprises 4 exons and is on the antisense strand of gene encoding for TNF alpha induced protein 3 (TNFAIP3). AL357060.1 transcript has a length of 1959 bps. AC011511.2 lncRNA overlaps with intracellular adhesion molecule 1 (ICAM-1) on the antisense strand and regulates ICAM-1 expression. AC007389.1 is encoded by a 650 kb gene and comprises 10 exons. Both TNFAIP3 and ICAM-1 are associated with LPS exposure, airway inflammation and asthma.

Example 4—LncRNA AC011511.2 is Associated With Hyperreactive Mucous Response

To confirm the RNAseq results; the expression of AC011511.2 lncRNA in the in-vitro model of hyperreactive mucous response was interrogated. The secondary LPS challenge augmented a more than 6-fold increase in this lncRNA levels in L/10 human AECs compared to controls (FIG. 3A). The sequencing and annotation analysis revealed that this lncRNA in 32.4 kb long with 3 exons and 2 introns and several splicing sites (FIG. 3B). This lncRNA had the negligible protein coding potential with a Fickett Testcode score of 0.27327 with coding probability 0.197913. A qPCR analysis was then performed to analyze the expression of this lncRNA by targeting each exon in LPS treated human AECs. Both exon1 (FIG. 3C) and exon 2 (FIG. 3D) showed induced expression whereas there was no significant induction in exon 3 transcript (FIG. 3E), indicative of splice variants. These data suggest that this lncRNA transcripts specific exon 1 and 2 might be implicated in the LPS-induced mucous response.

Example 5—the Expression Kinetics of LncRNAs in Primary Human AECs Following LPS Treatment AECs differentiated in the ALI on a transwell membrane are treated with LPS (100 ng/ml) or house-dust mite (HDM) extract (50 ng/ml) (Greer labs). HDM extract is used as an alternative to LPS to analyze the AEC responses. HDM extract are also strongly associated with allergic asthma and are used routinely to model experimental asthma. Cells are analyzed for the expression of lncRNAs at 0, 0.5, 2, 6, 12 and 24 h post treatment. Secretory and ciliated cells are the main types of AECs along with basal cells. A relevant 3D in-vitro model of the hyperreactive mucous response was developed and characterized using differentiated human AECs. During epithelial cell differentiation, several genes showed ≥2-fold change, including secretory mucins (MUC5AC and MUC5B) and mucociliary regulatory genes (FoxJ1, TUBA3, SPDEF, FoxA3). These changes in gene expression are intrinsically controlled from within the epithelial cells to drive mucous cell differentiation.

Mucous differentiation and expression are analyzed by quantifying the MUC5AC mucin gene and protein levels by real-time qRT-PCR and immunostaining. The mucin regulatory transcription factors (SPDEF and FOXA3) are also analyzed by qRT-PCR and immunostaining. Transcripts levels of the AL357060.1, AC011511.2 and AC007389.1 lncRNAs are assessed by qRT-PCR. Primers spanning the various exons help determine the splice variant expression. Changes in the levels of inflammatory factors of AECs (e.g. CXCL8, IL-6 and IL-1b) are analyzed by qRT-PCR and correlated with the expression levels of these lncRNAs in this model. Analysis of the cell lysates and media superna-

Example 6—Determination of the Subcellular Localization of These lncRNAs

LncRNAs have been found in both the nucleus and cytoplasm and are shown to have broad regulatory functions at the epigenetic, transcriptional and post-transcriptional levels. The majority of the lncRNAs are located in the nucleus.

To determine the subcellular localization of these lncRNAs, the cytoplasmic and nuclear fractions are prepared from LPS treated AECs and subjected to RNA and protein isolation. Western blot analysis for actin and laminin B1 are used to analyze the separation of cytoplasmic and nuclear fractions. The lncRNA levels in each fraction are determined by qRT-PCR.

To complement these fractionation studies, FISH (Fluorescent in-situ hybridization) assay are performed using Alexa 550 labelled probes specifically recognizing these lncRNAs. The probe is designed targeting the highest-expressing exon for each lncRNA. The subcellular localization is analyzed using confocal and structured-illumination microscopy.

Although high-throughput RNA seq profiling identified these lncRNAs, there is no experimental evidence providing the exact sequence for characterization and further research. Therefore, rapid amplification of cDNA ends (RACE) was performed to determine the transcription initiation and termination sites.

RNA is isolated from human AECs. Using FirstChoice® RLM-RACE Kit (ThermoFisher), the 5' and 3' specific adapters and primers, the lncRNA transcripts are characterized. The full-length AL357060.1, AC011511.2 and AC007389.1 lncRNA transcripts are cloned into an expression plasmid, pCDNA5/TO mammalian expression vector (ThermoFisher) with tetracycline-regulatable promoter. Human AECs expressing these constructs are obtained and used to verify the subcellular localization. The cloned lncRNA plasmid constructs are also used for copy number analysis of each lncRNA.

Example 7—The Memory-Based Mucous Response

To analyze the memory-based mucous response, differentiated AECs are treated with LPS (100 ng/ml). The mucous response is assessed at day 1, 2, 5 and 10 to determine the complete resolution of mucous phenotype. For testing the recall mucous response, the time-point showing minimal mucous response is chosen and the differentiated human AECs are re-challenged with LPS at 0, 1, 10 and 100 ng/ml to determine the minimal threshold of LPS required to initiate mucous expression without affecting the ALI integrity as assessed by transepithelial electrical resistance (TEER) value analysis.

Example 8—The Binding Partners for AL357060.1 LncRNA

To determine the binding partners (transcripts or proteins) for AL357060.1 lncRNA, RNA pull down assay is performed. Briefly, biotinylated lncRNA is transcribed using Biotin RNA labeling kit (Sigma) according to manufacturer's instructions, treated with DNAse I (RNAse free) and purified using spin columns (Qiagen Inc). 2 μg of biotinylated-RNA are used to perform pull-down assay on HAEC sonicated cell lysates. The complex is pulled down using Dynabeads MyOne Streptavidin T1 (ThermoFisher). After thorough washing of the beads, lncRNA-interacting proteins are analyzed by SDS-PAGE and Coomassie staining. The protein bands are excised and identified by LC-MS mass spectroscopy. The pull-down products are subjected to nucleic acid purification to identify other RNA molecules in the complex by following RT-PCR and cDNA sequencing analysis. The binding sites and interactions identified are verified by genetic editing or competitive inhibition assays. Similar strategies are employed for other lncRNAs, AC011511.2 and AC007389.1.

As observed in the results with differentiated human AECs, a strong correlation of these lncRNAs with LPS-mediated AEC inflammatory as well as mucous response is observed. Also, direct LPS responses of AECs are assessed.

Example 9—Functional Characterization and Targeting of LncRNAs to Regulate Hyperreactive Mucous Response The key gene-regulating mechanisms ascribed to lncRNAs include modular scaffold or molecular sponges that control protein complex formation, and binding to transcription factors and RNA polymerase II. In the cytoplasm, lncRNA scaffolds have been demonstrated to impact gene expression by regulating the stability, degradation, translational activation, and translational repression of the mRNA. LncRNAs can influence gene regulation by acting as decoys to sequester protein and RNA. Some lncRNAs have intrinsic catalytic activities and serve as signaling molecules to regulate gene expression in a temporal and spatial manner. In addition, lncRNA can act as guide lncRNA to recruit chromatin modifying enzymes to target genes via cis or trans regulatory mechanisms. Therefore, differentiated human AECs from asthmatics and control subjects are employed to test the utility of specific intervention strategies in regulating LPS-mediated mucous response. The AECs from asthmatic and non-asthmatic controls with and without LPS challenge are analyzed. Experiments are performed in-vitro to test whether modulating these lncRNAs can help regulate hyperreactive mucous response in the asthmatic AECs.

The airway epithelium of subjects was examined with reported asthma regarding the expression of MUC5AC and lncRNA AC011511.2 expression. The airway sections from age- and gender-matched asthmatics and controls (n=4) were analyzed for MUC5AC immunostaining and showed increased levels in asthmatic airways (FIG. 4A) and the RNA from AECs showed higher expression of lncRNA AC011511.2 (FIG. 4B) in asthmatics compared to controls suggesting that this lncRNA may be associated with CMH and asthma.

AECs from asthmatics and non-asthmatic subjects (Lonza Walkersville Inc.) are differentiated on transwells and treated with LPS (100 ng/ml). The LPS treated and non-treated AECs are compared with asthmatic patients. AECs from each subject are cultured and used for studies and snap-frozen before culture for RNA and protein analyses. Briefly, primary epithelial cells are grown at the ALI. Human AECs take approximately 3 weeks to differentiate into ciliated and mucous cells. Human AECs from these two groups are treated with LPS on day 1 and day 10 after complete differentiation to compare and contrast the hyperreactive mucous response in these subjects. The apical and basal media are be collected and stored in aliquots at −80° C. for future analysis of inflammatory factors secreted by these cells before, during and after the treatments. Differentiated cells are counted using immunostaining of mucous (MUC5AC+) cells; and changes in mucin gene expression are measured.

Figure 5C:
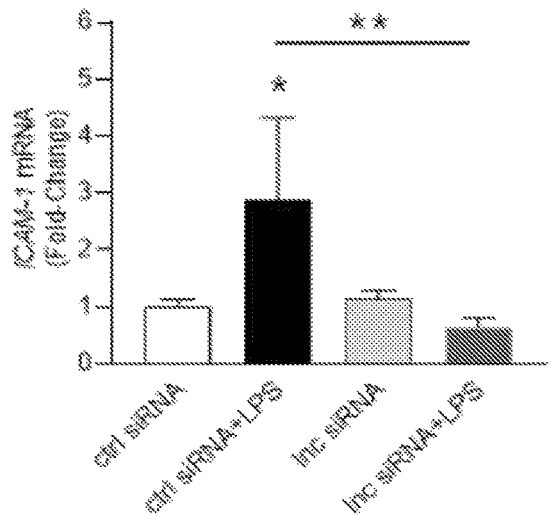
Figure 5D:
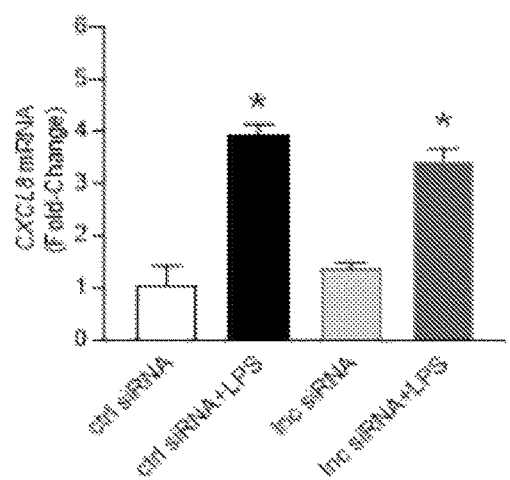

Differentiated AECs from asthmatics showed elevated mucous expression and associated increase in lncRNA expression (FIG. 4). These findings highlight that there are intrinsic alterations in lncRNAs between asthmatic and non-asthmatics. To further interrogate the role of lncRNA AC011511.2, human AECs were pre-incubated with various siRNAs targeting this lncRNA and found that X1 siRNA specifically downregulated its expression by more than 5-fold (FIG. 5A). The human AECs were then challenged with LPS (100 ng/ml) or Saline (0) on day 10 and cells were harvested 24 h later for analysis. The LPS challenge augmented the lncRNA levels in human AECs but it was completely blocked in the human AECs pretreated with siRNA (FIG. 5A). When checked for other epithelial secreted factors, the lnc siRNA-treated cells showed an attenuated expression of IL-6 (FIG. 5B) and ICAM-1 (FIG. 5C), however, there was no effect on the CXCL-8 levels (FIG. 5D). These data suggest that the suppression of lncRNA may help modulate AEC responses.

AECs from asthmatics are used to investigate the mucous responses. The target sequences are edited using CRISPR interference (CRISPRi) technology with constructs designed commercially (Cellecta Inc., Mountain View, Calif.). The effect on the AEC inflammatory responses and mucous responses is assessed.

To validate the specificity of the lncRNA, rescue experiments are performed. The AECs with attenuated expression of lncRNAs are transfected with lncRNA overexpressing lentiviral constructs (OrigeneInc). Similarly, the lncRNA AL357060.1 is targeted by abovementioned methodologies and determine that hyperreactive mucous response can be downregulated in asthmatic AECs.

Contrasting differences in lncRNA levels were identified in asthmatics AECs from that in non-asthmatics. The data obtained are helpful in improving the understanding of mucous cell biology and provide valuable information about the role of immunologic memory of AECs in mucous differentiation and airway inflammation in allergic asthma. Genetic targeting experiments for the lncRNAs provide novel intervention strategies against airway inflammation. To target the 3D structural motif of the lncRNAs, locked nucleic acids are employed to block lncRNAs.

Example 10—Mucous Dysregulation and COPD Severity

Tissue sections from chronic bronchitics with increased mucous expression demonstrated a higher expression of lncRNA AC011511.2 when compared to age- and gender-matched controls. Demographics of COPD subjects studied are shown in Table 4.

TABLE 4

|  | GOLD 1 (n = 6) | GOLD 2 (n = 7) | GOLD 3 (n = 7) | GOLD 4 (n = 6) |
|---|---|---|---|---|
| Age* | 65.2 ± 3.2 | 62.4 ± 4.1 | 69.3 ± 2.4 | 59.7 ± 2.7 |
| Gender, M/F | 5/1 | 4/3 | 1/6 | 3/4 |
| Smoking in PY* | 42.5.1 ± 18.8 (2) | 22.4 ± 13.0 (4) | 40.5 ± 12.0 (2) | 37.0 ± 3.8 (5) |
| Stop Smoking (Y)* | 20.4 ± 14.1 (2) | 22.9 ± 12.8 (4) | 14.9 ± 1.8 (2) | 13.2 ± 3.9 (5) |

Figure 6A:
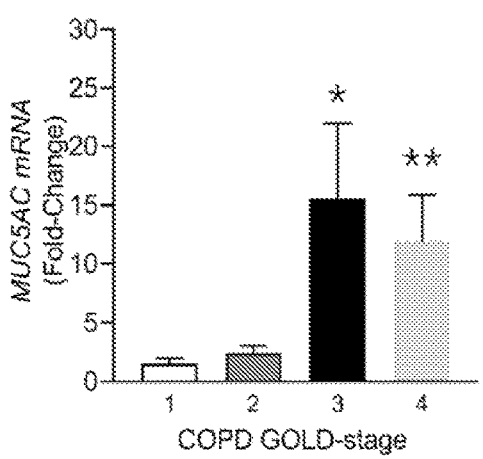
FIGS. 6A-6B show the increased expression of mucin MUC5AC and associated increase in lncRNA AC011511.2 among COPD subjects. Changes in MUC5AC mRNA (6A) and lncRNA AC011511.2 (6B) levels in COPD subjects of 1-4 GOLD stage severity as determined by qRT-PCR assay.
Figure 6B:
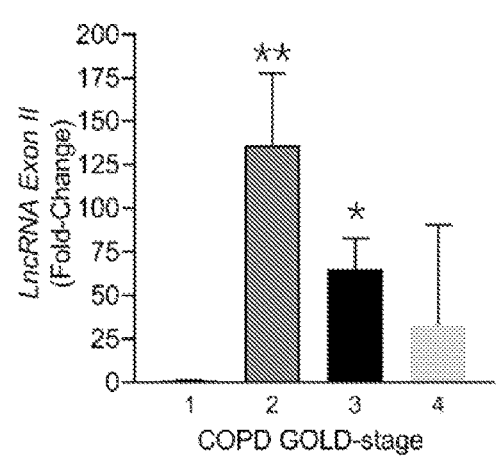

Lung tissues of COPD subjects were collected. qRT-PCR assay was used to determine the expression of mucin MUC5AC and lncRNA AC011511.2 among COPD subjects. The result shows that the expression levels of mucin MUC5AC (FIG. 6A) and lncRNA AC011511.2 (FIG. 6B) increase with the GOLD stage severity of COPD subjects. Significant increase in the expression of mucin MUC5AC was observed in COPD GOLD-stage 3 and 4 patients and significant increase in the expression of lncRNA AC011511.2 was observed in COPD GOLD-stage 2 and 3 patients.

Figure 7A:
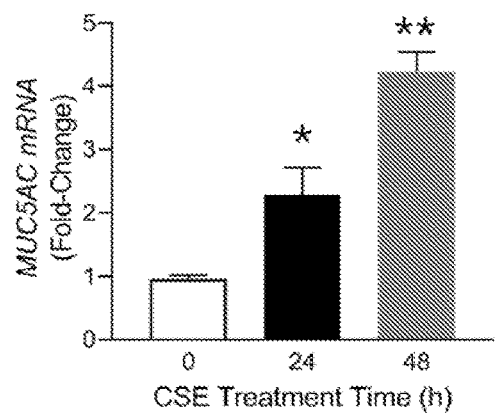
FIGS. 7A-7B show the cigarette smoke extract (CSE) treatment of human airway epithelial cells induces mucin MUC5AC and lncRNA AC011511.2 levels. Changes in MUC5AC mRNA (7A) and lncRNA AC011511.2 (7B) levels at 0, 24 and 48 h post CSE treatment (10 µg/ml) of HAECs as determined by qRT-PCR assay.
Figure 7B:
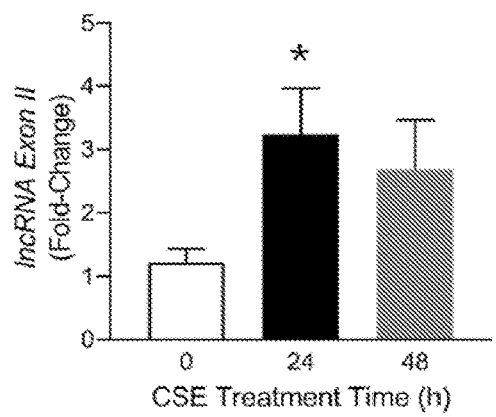
Figure 8A:
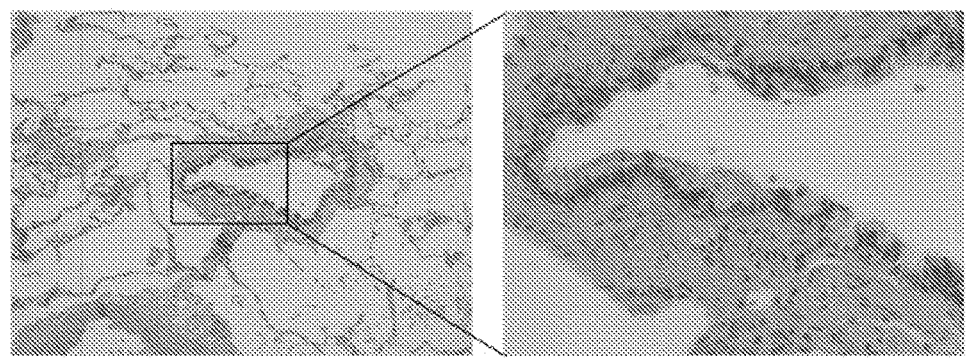
FIGS. 8A-8D show that mucous dysregulation is strongly associated with the GOLD (Global initiative of COPD) stage severity among COPD patients: (8A) GOLD 1, (8B) GOLD 2, (8C) GOLD 3, and (8D) GOLD 4. The small airway sections obtained from the Lung Tissue Research Consortium (NHLBI, NIH) were stained with Alcian Blue (for mucopolysaccharides) and H&E. Magnifications: left panels—100×; right panels×400×.
Figure 8B:
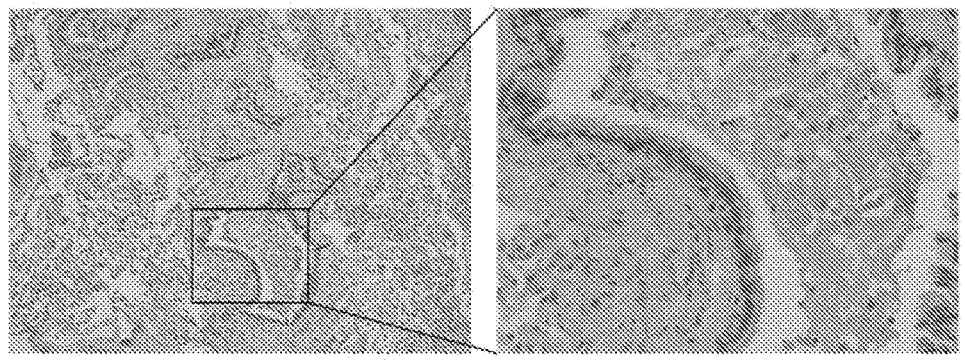
Figure 8C:
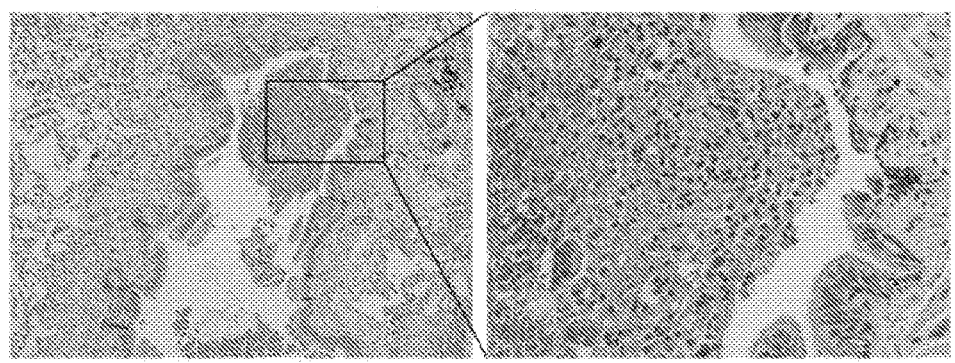
Figure 8D:
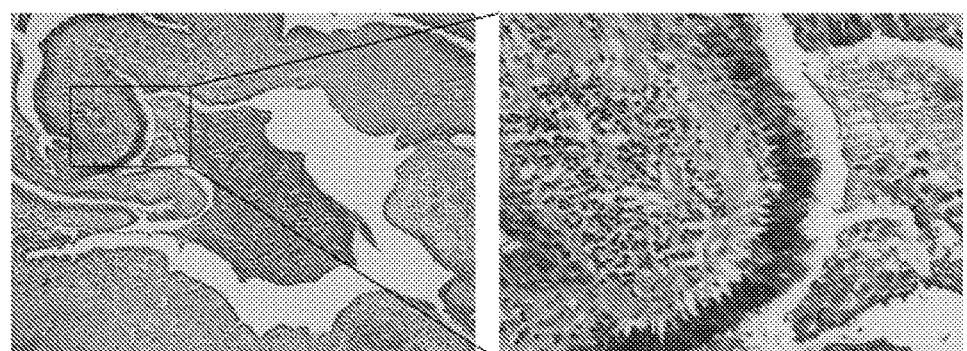

To determine the effect of cigarette smoke extract (CSE) on human airway epithelial cells (HAECs), HAECs are treated with CSE (10 µg/ml) for 24 and 48 hours. qRT-PCR assay is then used to determine the expression levels of mucin MUC5AC and lncRNA AC011511.2. The results show that CSE treatment induces the expression of mucin MUC5AC and lncRNA AC011511.2 levels in HAECs (FIG. 7).

Further, airway sections from age- and gender-matched chronic bronchitics and controls (n=4) that show increased mucous in airways (FIGS. 8A-8D) shows higher expression of lncRNA AC011511.2 compared to controls, suggesting that this lncRNA may be associated with chronic bronchitis.

Example 11—Differential LncRNA Upregulation in COPD Subjects

Figure 9D:
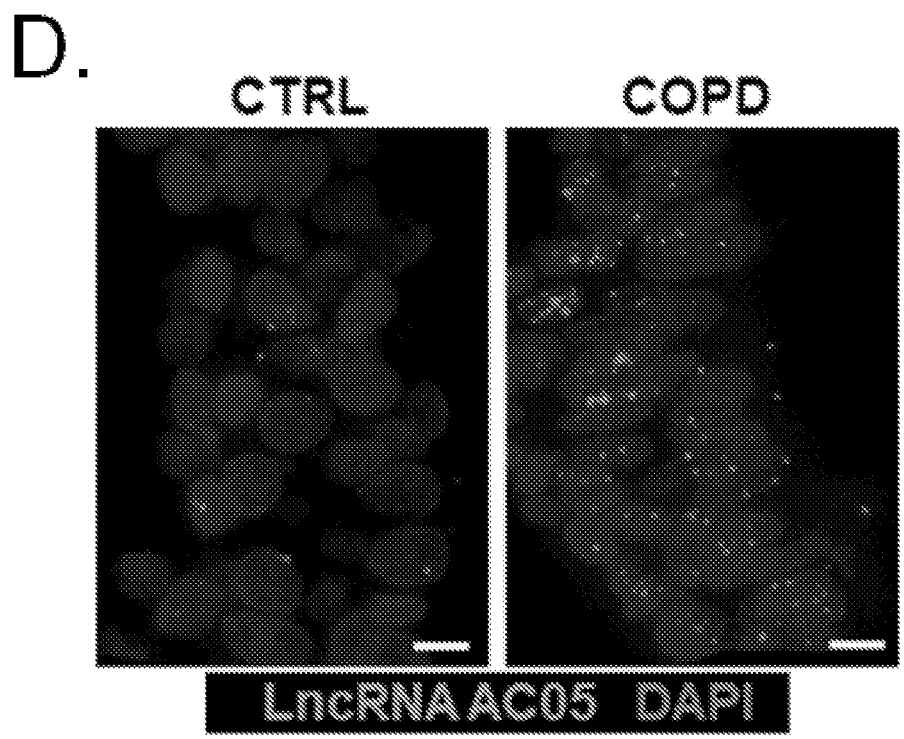

The airway epithelium of archived lung tissues from COPD subjects was examined for the lncRNA AL357060.1 or AL35 and AC011511.2 or AC05 expression and compared with non-COPD controls. The frozen airway tissues from age- and smoking history-matched subjects (FIG. 9A, see demographics) were screened for these lncRNA transcript levels by FAM-based qPCR. There were increased levels of AL35 (FIG. 9B) and AC05 (FIG. 9C) transcripts in COPD subjects with more than 50-fold higher expression of AC05 transcripts.

Figure 9E:
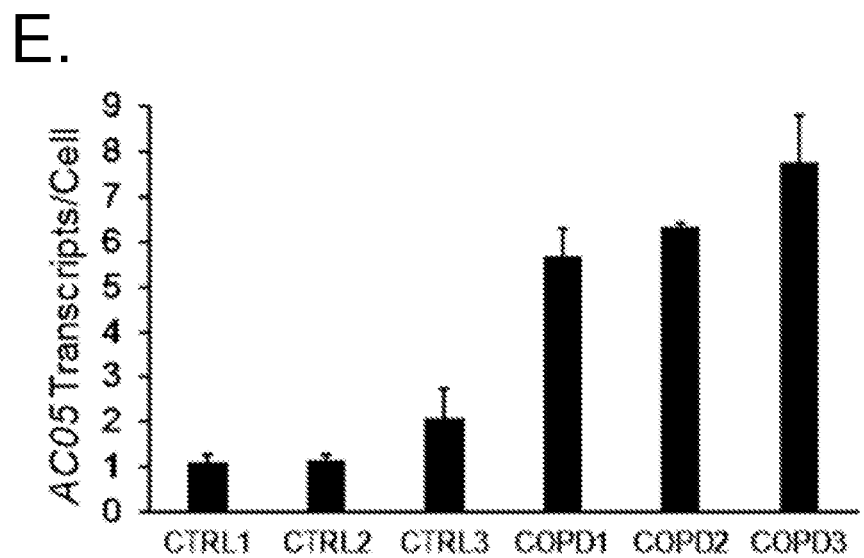
Figure 9F:
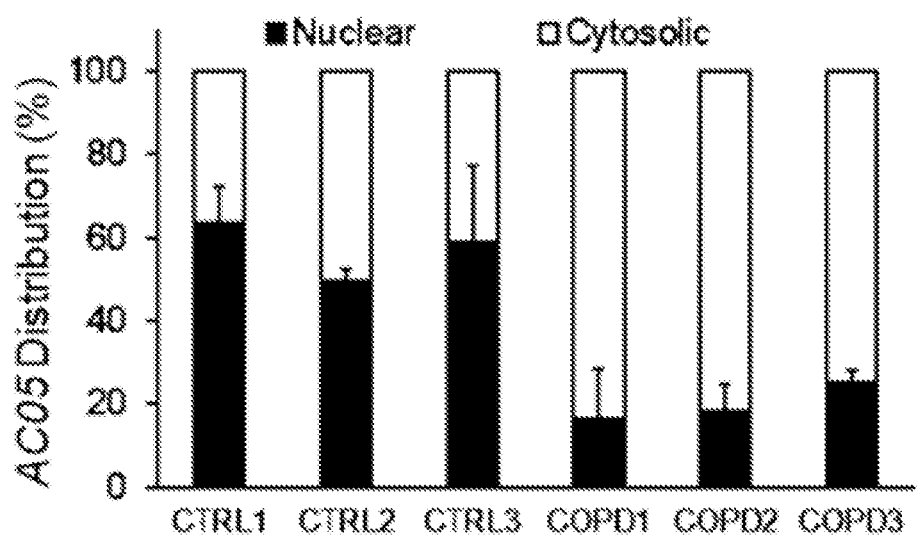

To identify the cell-specific expression of lncRNA AC05 transcripts, a highly sensitive probe for FISH (Fluorescent In-situ Hybridization)-based detection was developed using RNAscope® (ACD Biotechne) technology. There was a significant induction of lncRNA AC05 transcripts in bronchial airway epithelium of COPD subjects (FIG. 9D), compared to submucosal tissue, with a three-fold higher number of lncRNA molecules per epithelial cell (FIG. 9E) compared to controls. Using a high-resolution structured illumination imaging technique, the subcellular distribution of this transcript was quantified. The AC05 transcripts were primarily (>80%) present in the cytosolic region (FIG. 9F) than the nucleus, suggesting that AC05 lncRNA could be involved in regulating transcriptional or post-transcriptional processes. These findings suggest that lncRNA AL35 and AC05 may be associated with the COPD pathogenesis and could be useful targets for improving the COPD management strategies.

What is claimed is:

1. A pharmaceutical composition comprising one or more inhibitors of a long noncoding RNA (lncRNA) and a pharmaceutically acceptable carrier, the inhibitor comprising a siRNA selected from
   i) X1 siRNA (6-30): SEQ ID NOs: 4-5;
   ii) X2-A siRNA (26-55): SEQ ID NOs: 6-7;
   iii) X2-B siRNA (35-59): SEQ ID NOs: 8-9; and
   iv) X3 siRNA (37-61): SEQ ID NOs: 10-11.

2. The pharmaceutical composition of claim 1, the lncRNA being lncRNA AC011511.2 as set forth in SEQ ID NOs: 1-3.

3. The pharmaceutical composition of claim 1, the inhibitor of the lncRNA consisting of i) X1 siRNA (6-30): SEQ ID NOs: 4-5, ii) X2-A siRNA (26-55): SEQ ID NOs: 6-7, iii) X2-B siRNA (35-59): SEQ ID NOs: 8-9, or iv) X3 siRNA (37-61): SEQ ID NOs: 10-11.

4. A method for reducing inflammation in airway epithelial cells (AECs) in a subject, the method comprising administering to the subject in need of the reduction the pharmaceutical composition of claim 1.

5. The method of claim 4, the subject being a human.

6. The method of claim 4, the lncRNA being AC011511.2 as set forth in SEQ ID NOs: 1-3.

7. The method of claim 4, the inhibitor of the lncRNA comprising X1 siRNA (6-30): SEQ ID NOs: 4-5 or X2-A siRNA (26-55): SEQ ID NOs: 6-7.

8. The method of claim 4, the inhibitor of the lncRNA consisting of i) X1 siRNA (6-30): SEQ ID NOs: 4-5; ii) X2-A siRNA (26-55): SEQ ID NOs: 6-7; iii) X2-B siRNA (35-59): SEQ ID NOs: 8-9; or iv) X3 siRNA (37-61): SEQ ID NOs: 10-11.

9. The method of claim 4, the administration being oral, nasal, intravenous, intraperitoneal, or intramuscular administration.

10. The method of claim 4, the inflammation being associated with asthma, chronic obstructive pulmonary diseases (COPD) and Chronic mucus hypersecretion (CMH) pathogenesis.

11. The method of claim 4, further comprising a step of determining the level of lncRNA in an AEC sample of the subject prior to the administration and/or after the administration of the inhibitor.

12. A method for decreasing the expression of an lncRNA in a cell, the method comprising contacting the cell with the pharmaceutical composition of claim 1.

13. The method of claim 12, the cell being an AEC.

14. The method of claim 12, the inhibitor of the lncRNA comprising SEQ ID NOs: 10 and 11.

15. A method for reducing a mucous response in the airway of a subject, the method comprising administering to the subject the pharmaceutical composition of claim 1.

16. The method of claim 15, the inhibitor of the lncRNA consisting of i) X1 siRNA (6-30): SEQ ID NOs: 4-5; ii) X2-A siRNA (26-55): SEQ ID NOs: 6-7; iii) X2-B siRNA (35-59): SEQ ID NOs: 8-9; or iv) X3 siRNA (37-61): SEQ ID NOs: 10-11.

17. The method of claim 15, the lncRNA being AC011511.2 as set forth in SEQ ID NOs: 1-3.

18. The method of claim 15, the inhibitor of the lncRNA being X1 siRNA (6-30): SEQ ID NOs: 4-5.

19. The method of claim 15, the administration being oral, nasal, intravenous, intraperitoneal, or intramuscular administration.

20. The method of claim 15, the mucous response being associated with asthma, chronic obstructive pulmonary diseases (COPD) and Chronic mucus hypersecretion (CMH) pathogenesis.

* * * * *

SEQUENCE LISTING

<160> NUMBER OF SEQ ID NOS: 33

<210> SEQ ID NO 1
<211> LENGTH: 141
<212> TYPE: DNA
<213> ORGANISM: Homo sapiens

<400> SEQUENCE: 1
ggaggataca acaggcggtg aggattgcat taggtccatg gccccctgccc ccacccagct    60 ctgcccgccg gctcactcac agagcacatt cacggtcacc ttgcgggtga cctccccttg   120
agtgctcctg gcccgacaga g                                             141

<210> SEQ ID NO 2
<211> LENGTH: 217
<212> TYPE: DNA
<213> ORGANISM: Homo sapiens

<400> SEQUENCE: 2
gaagtcactc tgaaaactca ggtttacaca acatctactt gtacaatcaa gcacacactc    60
tcaggctgca tgaagtactg tcgcagacag gactgcaaac cctctcaggg gtgagaatgg   120
ctggcagcag tgctcaggag agggatgtgg caggagtcag ctcctaggaa gtgccagcgc   180
ccacgcacct gtgagctcct ggagtctgac tcaccgg                            217

<210> SEQ ID NO 3
<211> LENGTH: 560
<212> TYPE: DNA
<213> ORGANISM: Homo sapiens

<400> SEQUENCE: 3
gtggagaaac ggaggctgta gaaatacagc actttcccaa gggtacaagc ccaaagtcat    60
cgtgactcct gaaatcccgc tcttcatccc tctgccactc agttcaccat tacagccctc   120
gctcacctgg gcgcggtggc gaaaacatcg gggtgcaggt cggccaggcc cacgcgctcc   180
tgctcgaagc cccgcaagga ctcgacccag gcctgcactg ggcgtcgatg agtgggtacc   240
gggagctcga ctttgcgcag cacgggctcc gggagacctg gagcgattgc gggggtcaga   300
ggttagggtc aagggtcaga cctctctgtc gccgcccctc ctggagccac cccggttgcc   360
ttaccctcgc tcgccacctg ctccgggttc tcggtcgcac gcgctgcctc ttccgccagg   420
gaactcaggc cctgcaaggg ttgggcgaaa gtgagagacg accccctggac acccccaaat   480 ttcatccttc gaccacgcct ccagccctg gcctcacctg gctgccggta ggccgaagcc   540
aggcccgcgc cccggcccgg                                               560

<210> SEQ ID NO 4
<211> LENGTH: 25
<212> TYPE: DNA
<213> ORGANISM: Artificial sequence
<220> FEATURE:
<223> OTHER INFORMATION: siRNA targeting lncRNA AC011511.2

<400> SEQUENCE: 4
auacaacagg cggugaggau ugcat                                          25

<210> SEQ ID NO 5
<211> LENGTH: 28
<212> TYPE: RNA
<213> ORGANISM: Artificial sequence
<220> FEATURE:
<223> OTHER INFORMATION: siRNA targeting lncRNA AC011511.2

```
<400> SEQUENCE: 5
augcaauccu caccgccugu uguaucrc                                          28

<210> SEQ ID NO 6
<211> LENGTH: 25
<212> TYPE: RNA
<213> ORGANISM: Artificial sequence
<220> FEATURE:
<223> OTHER INFORMATION: siRNA targeting lncRNA AC011511.2

<400> SEQUENCE: 6
acacaacauc uacuuguaca aucaa                                             25

<210> SEQ ID NO 7
<211> LENGTH: 27
<212> TYPE: RNA
<213> ORGANISM: Artificial sequence
<220> FEATURE:
<223> OTHER INFORMATION: siRNA targeting lncRNA AC011511.2

<400> SEQUENCE: 7
uugauuguac aaguagaugu uguguaa                                           27

<210> SEQ ID NO 8
<211> LENGTH: 25
<212> TYPE: DNA
<213> ORGANISM: Artificial sequence
<220> FEATURE:
<223> OTHER INFORMATION: siRNA targeting lncRNA AC011511.2

<400> SEQUENCE: 8
cuacuuguac aaucaagcac acact                                             25

<210> SEQ ID NO 9
<211> LENGTH: 27
<212> TYPE: RNA
<213> ORGANISM: Artificial sequence
<220> FEATURE:
<223> OTHER INFORMATION: siRNA targeting lncRNA AC011511.2

<400> SEQUENCE: 9
agugugugcu ugauuguaca aguagau                                           27

<210> SEQ ID NO 10
<211> LENGTH: 25
<212> TYPE: DNA
<213> ORGANISM: Artificial sequence
<220> FEATURE:
<223> OTHER INFORMATION: siRNA targeting lncRNA AC011511.2

<400> SEQUENCE: 10
ccaaggguac aagcccaaag ucatc                                             25

<210> SEQ ID NO 11
<211> LENGTH: 27
<212> TYPE: RNA
<213> ORGANISM: Artificial sequence
<220> FEATURE:
<223> OTHER INFORMATION: siRNA targeting lncRNA AC011511.2

<400> SEQUENCE: 11
gaugacuuug ggcuuguacc cuuggga                                           27

<210> SEQ ID NO 12
```

```
<211> LENGTH: 20
<212> TYPE: DNA
<213> ORGANISM: Artificial sequence
<220> FEATURE:
<223> OTHER INFORMATION: primer

<400> SEQUENCE: 12
cggtgaggat tgcattaggt                                           20

<210> SEQ ID NO 13
<211> LENGTH: 20
<212> TYPE: DNA
<213> ORGANISM: Artificial sequence
<220> FEATURE:
<223> OTHER INFORMATION: primer

<400> SEQUENCE: 13
cgtgaatgtg ctctgtgagt                                           20

<210> SEQ ID NO 14
<211> LENGTH: 19
<212> TYPE: DNA
<213> ORGANISM: Artificial sequence
<220> FEATURE:
<223> OTHER INFORMATION: primer

<400> SEQUENCE: 14
caacaggcgg tgaggattg                                            19

<210> SEQ ID NO 15
<211> LENGTH: 19
<212> TYPE: DNA
<213> ORGANISM: Artificial sequence
<220> FEATURE:
<223> OTHER INFORMATION: primer

<400> SEQUENCE: 15
gcaaggtgac cgtgaatgt                                            19

<210> SEQ ID NO 16
<211> LENGTH: 25
<212> TYPE: DNA
<213> ORGANISM: Homo sapiens

<400> SEQUENCE: 16
atacaacagg cggtgaggat tgcat                                     25

<210> SEQ ID NO 17
<211> LENGTH: 25
<212> TYPE: DNA
<213> ORGANISM: Homo sapiens

<400> SEQUENCE: 17
acacaacatc tacttgtaca atcaa                                     25

<210> SEQ ID NO 18
<211> LENGTH: 25
<212> TYPE: DNA
<213> ORGANISM: Homo sapiens

<400> SEQUENCE: 18
ctacttgtac aatcaagcac acact                                     25

<210> SEQ ID NO 19
<211> LENGTH: 25
```

```
<212> TYPE: DNA
<213> ORGANISM: Homo sapiens

<400> SEQUENCE: 19
ccaagggtac aagcccaaag tcatc                                           25

<210> SEQ ID NO 20
<211> LENGTH: 25
<212> TYPE: DNA
<213> ORGANISM: Homo sapiens

<400> SEQUENCE: 20
ctctgcccgc cggctcactc acaga                                           25

<210> SEQ ID NO 21
<211> LENGTH: 25
<212> TYPE: DNA
<213> ORGANISM: Homo sapiens

<400> SEQUENCE: 21
ctctcagggg tgagaatggc tggca                                           25

<210> SEQ ID NO 22
<211> LENGTH: 25
<212> TYPE: DNA
<213> ORGANISM: Homo sapiens

<400> SEQUENCE: 22
gctccgggag acctggagcg attgc                                           25

<210> SEQ ID NO 23
<211> LENGTH: 1959
<212> TYPE: DNA
<213> ORGANISM: Homo sapiens

<400> SEQUENCE: 23
actgcttttc tgagaggcca ggtggcagga tgtgggacga ctccagctga caaagacagt     60
ctaaccgtgg ggtaggggct ggagcagggg ccagcgaccc acgtctacat gcatacttct    120
cttacactgc tgctactgga aaagctgaac cccgcgccag gaccccagcc cctgcaagg    180
acccgtgagc gtctgggaag ctgtctctgg gactgaagcc ccccacctcc gccgggctgg    240
cggccactgc ggtaccctac gccccgtcgg gctggtcctg cacaatttgg gaaaaagccg    300
cagcgcttct gcaaggtcta cgtggccatg agcatgcaac gcttggctcc aaaaaagaca    360
cgaaaggagc aaaagcgcca acgaccaccc gatcggaggg ccgaggggcg cctcttcacc    420
agtcagctgc agcttaagtt ccgtgcatta tctgaaagga acagctggct ggaggtatcc    480
agggctgtca ctccaacctc tgcagcagtg acctcaactc ccagcacttc aaaacccaga    540
cagaaacgtc caacaaactc ccagtccagg agcgctgcaa accaacgcc agttgttttt    600
ctgcagaaaa tcatcaactg tggagaagaa gagggaaat aagaaagaaa gaaaccccta    660
aaaaccaccc tggcgcccgg gcccgcaggc ctcgggccgg ctctgaaaag tttgggctgt    720
gcacgtgatg agcgcgtagg cgggagcccc agacaggacc cgggcgggca tttcgagaaa    780
aagcagcggt gacagccttt ggtccccatc tccattgttc ctgccagctc tggacccag    840
gctgcatgag acgtaggtcc caggggacac ccgaccccgt ggcccagtc ttagcttcca    900
ctgcccctat ctggctcatg tcttgctgtc tggtgtcatg aactgggagt gcagtaaaga    960
ggagtgacaa gcctgagggg ccacgttcat acctgccact gccaactgtc ctgatgtaac   1020
```

```
tgctttgtca tcttgcctgc caggatttgt gacaagggca agaatcttct gttccatatg   1080
caacatcttc tggcagcctt gtccttttc tgtccttgac gactacaata acaaacagct   1140
gttgccgagg cattgctgtt gacgtgttac ctttgaaacc tccctcctgt tatggaataa   1200
gcctcttcca gatcatggct cattatcatc tagtctgaca agcagccttg ttgccacgga   1260
gacccaaagg gatcaggcgt ggcatttgcc tgcatcatca cccctccag gggaactata    1320 aggactcttc tgtgcgtcat gcgtggctgt cctgggactg gctgccacca gacttttcct   1380
gcgggtaaaa cctaaacaaa tgatcagctg cagataatat caagacctct gtttgatatg   1440
ttaatagtga cagccagatt tccacaatta caacgaggt gggaagaaaa cactgtagtc    1500
accagacttg ggaggagagg gtttgtattc acataaacac aacctcacgt cactgcttgc   1560
caccacaaag ggctctgttc actgttttgt tctcaaagat catccttgcg ctcatcctct   1620
gatcttgaat ttctacataa ctttctcagt ttatatgccc tgtggcaagt gcagcaagca   1680
ctgtttcctg tttctaaact tgtagaaaat catccataca tcttacagtt gtcagtttta   1740
accagataac agtggcactt tgttgctgct tttttatctt tagcttaggt taacaggacc   1800
ctggaagtaa agttgttgat ttattcaata gagtattctc aattaatttg gctagatttc   1860
tacatgattc aaaatctaaa aaagtagaaa tgcatgctta catgtctaag gcctgaaaaa   1920
ttggtagtga catcccaaaa taaatgaagg ttttaaaac                          1959

<210> SEQ ID NO 24
<211> LENGTH: 592
<212> TYPE: DNA
<213> ORGANISM: Homo sapiens

<400> SEQUENCE: 24
actgcttttc tgagaggcca ggtggcagga tgtgggacga ctccagctga caaagacagt     60
ctaaccgtgg ggtaggggct ggagcagggg ccagcgaccc acgtctacat gcatacttct    120
cttacactgt tgctactgga aaagctgaac cccgcgccag gacccagcc ccctgcaagg     180 acccgtgagc gtctgggaag ctgtctctgg gactgaagcc cccacctcc gcgggctgg     240 cggccactgc ggtaccctac gccccgtcgg gctggtcctg cacaatttgg gaaaaagccg    300
cagcgcttct gcaaggtcta cgtggccatg agcatgcaac gcttggctcc aaaaaagaca    360
cgaaaggagc aaagcgccaa cgaccacccg atcggagggc cgaggggcg cctcttcacc     420 agtcagctgc agcttaagtt ccgtgcatta tctgaaagga acagctggct ggaggtatcc    480
agggctgtca ctccaacctc tgcagcagtg acctcaactc ccagcacttc aaaacccaga    540
cagaaacgtc caacaaactc ccagtccagg agcgctgcaa aaccaacgcc ag            592

<210> SEQ ID NO 25
<211> LENGTH: 302
<212> TYPE: DNA
<213> ORGANISM: Homo sapiens

<400> SEQUENCE: 25 ttgttttct gcagaaaatc atcaactgtg agaagaaga agggaaataa gaaagaaaga       60
aaaccctaaa aaccaccctg gcgcccgggc ccgcaggcct cgggccggct ctgaaaagtt    120
tgggctgtgc acgtgatgag cgcgtaggcg ggagcccag acaggacccg gcgggcatt     180 tcgagaaaaa gcagcggtga cagccttttgg tccccatctc cattgttcct gccagctctg    240
gaccccaggc tgcatgagac gtaggtccca ggggacaccc gaccccgtgg ccccagtctt    300
ag                                                                 302
```

<210> SEQ ID NO 26
<211> LENGTH: 162
<212> TYPE: DNA
<213> ORGANISM: Homo sapiens

<400> SEQUENCE: 26
cttccactgc ccctatctgg ctcatgtctt gctgtctggt gtcatgaact gggagtgcag      60
taaagaggag tgacaagcct gaggggccac gttcatacct gccactgcca actgtcctga     120
tgtaactgct ttgtcatctt gcctgccagg atttgtgaca ag                        162

<210> SEQ ID NO 27
<211> LENGTH: 903
<212> TYPE: DNA
<213> ORGANISM: Homo sapiens

<400> SEQUENCE: 27
ggcaagaatc ttctgttcca tatgcaacat cttctggcag ccttgtcctt tttctgtcct      60
tgacgactac aataacaaac agctgttgcc gaggcattgc tgttgacgtg ttacctttga     120
aacctccctc ctgttatgga ataagcctct tccagatcat ggctcattat catctagtct     180
gacaagcagc cttgttgcca cggagaccca agggatcag gcgtggcatt tgcctgcatc      240 atcacccccct ccaggggaac tataaggact cttctgtgcg tcatgcgtgg ctgtcctggg    300
actggctgcc accagacttt tcctgcgggt aaaacctaaa caatgatca gctgcagata      360 atatcaagac ctctgtttga tatgttaata gtgacagcca gatttccaca attaacaacg     420
aggtgggaag aaaacactgt agtcaccaga cttgggagga gagggtttgt attcacataa     480
acacaacctc acgtcactgc ttgccaccac aaagggctct gttcactgtt ttgttctcaa     540
agatcatcct tgcgctcatc ctctgatctt gaatttctac ataactttct cagtttatat     600
gccctgtggc aagtgcagca agcactgttt cctgtttcta aacttgtaga aaatcatcca     660
tacatcttac agttgtcagt tttaaccaga taacagtggc actttgttgc tgcttttta     720 tctttagctt aggttaacag gaccctggaa gtaaagttgt tgatttattc aatagagtat     780
tctcaattaa tttggctaga tttctacatg attcaaaatc taaaaagta gaaatgcatg      840 cttacatgtc taaggcctga aaattggta gtgacatccc aaaataaatg aaggttttaa     900
aac                                                                   903

<210> SEQ ID NO 28
<211> LENGTH: 21
<212> TYPE: DNA
<213> ORGANISM: Artificial sequence
<220> FEATURE:
<223> OTHER INFORMATION: primer

<400> SEQUENCE: 28
tgaactggga gtgcagtaaa g                                                21

<210> SEQ ID NO 29
<211> LENGTH: 24
<212> TYPE: DNA
<213> ORGANISM: Artificial sequence
<220> FEATURE:
<223> OTHER INFORMATION: probe sequence

<400> SEQUENCE: 29
ttcatacctg ccactgccaa ctgt                                             24

```
<210> SEQ ID NO 30
<211> LENGTH: 22
<212> TYPE: DNA
<213> ORGANISM: Artificial sequence
<220> FEATURE:
<223> OTHER INFORMATION: primer

<400> SEQUENCE: 30
ggcaagatga caaagcagtt ac                                              22

<210> SEQ ID NO 31
<211> LENGTH: 22
<212> TYPE: DNA
<213> ORGANISM: Artificial sequence
<220> FEATURE:
<223> OTHER INFORMATION: primer

<400> SEQUENCE: 31
caattaacaa cgaggtggga ag                                              22

<210> SEQ ID NO 32
<211> LENGTH: 24
<212> TYPE: DNA
<213> ORGANISM: Artificial sequence
<220> FEATURE:
<223> OTHER INFORMATION: probe sequence

<400> SEQUENCE: 32
accagacttg ggaggagagg gttt                                            24

<210> SEQ ID NO 33
<211> LENGTH: 22
<212> TYPE: DNA
<213> ORGANISM: Artificial sequence
<220> FEATURE:
<223> OTHER INFORMATION: primer

<400> SEQUENCE: 33
gtgacgtgag gttgtgttta tg                                              22
```